United States Patent
Takenaka et al.

(10) Patent No.: US 7,098,019 B2
(45) Date of Patent: Aug. 29, 2006

(54) DNA FOR ENCODING D-HYDANTOIN HYDROLASES, DNA FOR ENCODING N-CARBAMYL-D-AMINO ACID HYDROLASES, RECOMBINANT DNA CONTAINING THE GENES, CELLS TRANSFORMED WITH THE RECOMBINANT DNA, METHODS FOR PRODUCING PROTEINS UTILIZING THE TRANSFORMED CELLS AND METHODS FOR PRODUCING D-AMINO ACIDS

(75) Inventors: Yasuhiro Takenaka, Kanagawa (JP); Ikuo Kira, Kanagawa (JP); Kenzo Yokozeki, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 425 days.

(21) Appl. No.: 10/190,471

(22) Filed: Jul. 9, 2002

(65) Prior Publication Data

US 2003/0113880 A1 Jun. 19, 2003

(30) Foreign Application Priority Data

Jul. 10, 2001 (JP) .............................. 2001-209713

(51) Int. Cl.
*C12N 15/55* (2006.01)
*C12N 9/78* (2006.01)
*C12P 13/04* (2006.01)

(52) U.S. Cl. .................. 435/227; 435/106; 435/252.3; 536/23.2

(58) Field of Classification Search ................ 435/227, 435/252.3, 106; 536/23.2
See application file for complete search history.

(56) References Cited

U.S. PATENT DOCUMENTS

| 5,523,224 | A | * | 6/1996 | Burtscher et al. | ........... 435/231 |
| 5,679,571 | A | * | 10/1997 | Burtscher et al. | ........... 435/325 |
| 6,566,105 | B1 | * | 5/2003 | Grifantini et al. | .......... 435/106 |
| 6,800,465 | B1 | * | 10/2004 | Politino et al. | ............. 435/106 |

FOREIGN PATENT DOCUMENTS

| JP | 56-089088 | 7/1979 |
| JP | 3-19696 | 1/1991 |

* cited by examiner

*Primary Examiner*—Charles L. Patterson, Jr.
(74) *Attorney, Agent, or Firm*—Oblon, Spivak, McClelland, Maier & Neustadt, P.C.

(57) ABSTRACT

DNA for encoding a protein having D-hydantoinase activity which has a base sequence represented by Sequence ID No. 1 in the Sequence Listing. DNA for encoding a protein having D-carbamylase activity which has a base sequence represented by Sequence ID No. 3 in the Sequence Listing.

44 Claims, 1 Drawing Sheet

ORF1: D-CARBAMYLASE GENE
ORF2: D-HYDANTOINASE GENE

SEQUENCE LISTING

```
<160> NUMBER OF SEQ ID NOS: 10

<210> SEQ ID NO 1
<211> LENGTH: 1389
<212> TYPE: DNA
<213> ORGANISM: Pasteurella pneumotropica
<220> FEATURE:
<221> NAME/KEY: CDS
<222> LOCATION: (1)..(1386)
<223> OTHER INFORMATION:

<400> SEQUENCE: 1 atg gat ctc atc gtc aag aac gga acg atc gtc acc gcc gcc ggc att        48
Met Asp Leu Ile Val Lys Asn Gly Thr Ile Val Thr Ala Ala Gly Ile
1               5                   10                  15 tcg cgc gcg gat ctc ggc gtc agg gac ggc aag atc gtc cag atc ggc        96
Ser Arg Ala Asp Leu Gly Val Arg Asp Gly Lys Ile Val Gln Ile Gly
                20                  25                  30 ggc gat ctc ggc gag gcg gcg cgc acg atc gac gcg acc ggc cgc tat       144
Gly Asp Leu Gly Glu Ala Ala Arg Thr Ile Asp Ala Thr Gly Arg Tyr
            35                  40                  45 gtc atg ccg ggc ggc gtc gac gtc cac acc cat atc gac tcc aac aac       192
Val Met Pro Gly Gly Val Asp Val His Thr His Ile Asp Ser Asn Asn
        50                  55                  60 atg gag acg aag tcg gcg gac gat ttc cgg acc ggc acg atc gcg gcg       240
Met Glu Thr Lys Ser Ala Asp Asp Phe Arg Thr Gly Thr Ile Ala Ala
65                  70                  75                  80 gcc tgt ggc ggc acg acg acg atc gtc gat ttc tgc gcc cag gac cgg       288
Ala Cys Gly Gly Thr Thr Thr Ile Val Asp Phe Cys Ala Gln Asp Arg
                85                  90                  95
```

-continued

| | |
|---|---|
| ggc ggc acg ctc gcc gag gcg atc gcc aaa tgg gac ggg cgg gcg gcc<br>Gly Gly Thr Leu Ala Glu Ala Ile Ala Lys Trp Asp Gly Arg Ala Ala<br>　　　　　100　　　　　　　　　105　　　　　　　　　110 | 336 |
| ggc aag gcg gcg atc gac tac ggc tac cat gtc atc gtg ctc gac atg<br>Gly Lys Ala Ala Ile Asp Tyr Gly Tyr His Val Ile Val Leu Asp Met<br>115　　　　　　　　　120　　　　　　　　　125 | 384 |
| aat ccc ggc gtg ttc gag gag ttg ctg acg ctg ccg gag cgt ggc att<br>Asn Pro Gly Val Phe Glu Glu Leu Leu Thr Leu Pro Glu Arg Gly Ile<br>　　130　　　　　　　　　135　　　　　　　　　140 | 432 |
| ccc tcc ttc aag gtg ttc atg gcc tat cgc ggc atg aac atg atc gac<br>Pro Ser Phe Lys Val Phe Met Ala Tyr Arg Gly Met Asn Met Ile Asp<br>145　　　　　　　　　150　　　　　　　　　155　　　　　　　　　160 | 480 |
| gac gtc acc ctg ctg aag acg ctg gag cag gcc aag cgc tcg ggg gcg<br>Asp Val Thr Leu Leu Lys Thr Leu Glu Gln Ala Lys Arg Ser Gly Ala<br>　　　　　165　　　　　　　　　170　　　　　　　　　175 | 528 |
| ctg gtc atg gtc cat gcc gag aac ggt gat gcg gcg gat ttc ctg cgc<br>Leu Val Met Val His Ala Glu Asn Gly Asp Ala Ala Asp Phe Leu Arg<br>　　　　　180　　　　　　　　　185　　　　　　　　　190 | 576 |
| gac aag ttc gtc gcc gag ggc aag acc tcg ccg aaa tac cac gcg ctc<br>Asp Lys Phe Val Ala Glu Gly Lys Thr Ser Pro Lys Tyr His Ala Leu<br>　　　　　195　　　　　　　　　200　　　　　　　　　205 | 624 |
| agc cgg ccg ccg cgg gtc gag gcc gag gcg acc gcg cgc gcc atc gcg<br>Ser Arg Pro Pro Arg Val Glu Ala Glu Ala Thr Ala Arg Ala Ile Ala<br>　　210　　　　　　　　　215　　　　　　　　　220 | 672 |
| atg gcc gag atc gtc ggc acc tcg atc tac atc gtg cac ctg acc tgc<br>Met Ala Glu Ile Val Gly Thr Ser Ile Tyr Ile Val His Leu Thr Cys<br>225　　　　　　　　　230　　　　　　　　　235　　　　　　　　　240 | 720 |
| gag gag gcg ctg gag gaa ctg atg cgc gcc aag gcg cgc ggc gtc gac<br>Glu Glu Ala Leu Glu Glu Leu Met Arg Ala Lys Ala Arg Gly Val Asp<br>　　　　　245　　　　　　　　　250　　　　　　　　　255 | 768 |
| gcg ctg gcc gag acc tgc acg cag tat ctc tac ctg acc aag gac gac<br>Ala Leu Ala Glu Thr Cys Thr Gln Tyr Leu Tyr Leu Thr Lys Asp Asp<br>　　　　　260　　　　　　　　　265　　　　　　　　　270 | 816 |
| ctc gac cgg ccg ggc ttc gag ggg gcg aag ttc gtc ttc acg ccg ccg<br>Leu Asp Arg Pro Gly Phe Glu Gly Ala Lys Phe Val Phe Thr Pro Pro<br>　　　　　275　　　　　　　　　280　　　　　　　　　285 | 864 |
| ccg cgc gag gtc aag gac cag gaa atc ctc tgg gag gcg ctg gcc aac<br>Pro Arg Glu Val Lys Asp Gln Glu Ile Leu Trp Glu Ala Leu Ala Asn<br>　　290　　　　　　　　　295　　　　　　　　　300 | 912 |
| cgc gtg ttc gag acg gtg tcg tcc gat cac tgc tcc tgg ctc tac aag<br>Arg Val Phe Glu Thr Val Ser Ser Asp His Cys Ser Trp Leu Tyr Lys<br>305　　　　　　　　　310　　　　　　　　　315　　　　　　　　　320 | 960 |
| ggc cac aag gat gag ggc ctg cac gat ttc cgg ctg atc ccg aac ggg<br>Gly His Lys Asp Glu Gly Leu His Asp Phe Arg Leu Ile Pro Asn Gly<br>　　　　　325　　　　　　　　　330　　　　　　　　　335 | 1008 |
| gcg ccc ggc gtc gag gag cgg atg atg atg gtc tac cag ggc gtc aac<br>Ala Pro Gly Val Glu Glu Arg Met Met Met Val Tyr Gln Gly Val Asn<br>　　　　　340　　　　　　　　　345　　　　　　　　　350 | 1056 |
| cag ggc cgc atc tcg ctg acc cag ttc gtc gac ctg gtg gcg acg cgg<br>Gln Gly Arg Ile Ser Leu Thr Gln Phe Val Asp Leu Val Ala Thr Arg<br>　　　　　355　　　　　　　　　360　　　　　　　　　365 | 1104 |
| ccg gcg cag gtg ttc ggc atg ttc ccg cag aag ggc acc atc gcc gtc<br>Pro Ala Gln Val Phe Gly Met Phe Pro Gln Lys Gly Thr Ile Ala Val<br>　　370　　　　　　　　　375　　　　　　　　　380 | 1152 |
| ggc tcc gac gcc gac ctc gtc atc tgg gac ccg gag gcg acg atg acg<br>Gly Ser Asp Ala Asp Leu Val Ile Trp Asp Pro Glu Ala Thr Met Thr<br>385　　　　　　　　　390　　　　　　　　　395　　　　　　　　　400 | 1200 |
| atc acc cag tcg gcg atg aac aac gcg atg gac tac tcg acc tat gag<br>Ile Thr Gln Ser Ala Met Asn Asn Ala Met Asp Tyr Ser Thr Tyr Glu | 1248 |

-continued

```
                    405                 410                 415
ggc cag gcc gtc aag gga atg ccc acg acg gtg gtg ctg cgc ggc aag   1296
Gly Gln Ala Val Lys Gly Met Pro Thr Thr Val Val Leu Arg Gly Lys
        420                 425                 430 gtc atc gtc gag gat cgc aac tat gtc ggc acg ccc ggc gaa ggg cgt   1344
Val Ile Val Glu Asp Arg Asn Tyr Val Gly Thr Pro Gly Glu Gly Arg
            435                 440                 445 ttc ctg cgg cgc gag cgc tac gcg cgt tcc ccg aag ctc gcc tga       1389
Phe Leu Arg Arg Glu Arg Tyr Ala Arg Ser Pro Lys Leu Ala
        450                 455                 460
```

<210> SEQ ID NO 2
<211> LENGTH: 462
<212> TYPE: PRT
<213> ORGANISM: Pasteurella pneumotropica

<400> SEQUENCE: 2

```
Met Asp Leu Ile Val Lys Asn Gly Thr Ile Val Thr Ala Ala Gly Ile
1               5                   10                  15

Ser Arg Ala Asp Leu Gly Val Arg Asp Gly Lys Ile Val Gln Ile Gly
            20                  25                  30

Gly Asp Leu Gly Glu Ala Ala Arg Thr Ile Asp Ala Thr Gly Arg Tyr
        35                  40                  45

Val Met Pro Gly Gly Val Asp Val His Thr His Ile Asp Ser Asn Asn
    50                  55                  60

Met Glu Thr Lys Ser Ala Asp Asp Phe Arg Thr Gly Thr Ile Ala Ala
65                  70                  75                  80

Ala Cys Gly Gly Thr Thr Thr Ile Val Asp Phe Cys Ala Gln Asp Arg
                85                  90                  95

Gly Gly Thr Leu Ala Glu Ala Ile Ala Lys Trp Asp Gly Arg Ala Ala
            100                 105                 110

Gly Lys Ala Ala Ile Asp Tyr Gly Tyr His Val Ile Val Leu Asp Met
        115                 120                 125

Asn Pro Gly Val Phe Glu Glu Leu Leu Thr Leu Pro Glu Arg Gly Ile
    130                 135                 140

Pro Ser Phe Lys Val Phe Met Ala Tyr Arg Gly Met Asn Met Ile Asp
145                 150                 155                 160

Asp Val Thr Leu Leu Lys Thr Leu Glu Gln Ala Lys Arg Ser Gly Ala
                165                 170                 175

Leu Val Met Val His Ala Glu Asn Gly Asp Ala Ala Asp Phe Leu Arg
            180                 185                 190

Asp Lys Phe Val Ala Glu Gly Lys Thr Ser Pro Lys Tyr His Ala Leu
        195                 200                 205

Ser Arg Pro Pro Arg Val Glu Ala Glu Ala Thr Ala Arg Ala Ile Ala
    210                 215                 220

Met Ala Glu Ile Val Gly Thr Ser Ile Tyr Ile Val His Leu Thr Cys
225                 230                 235                 240

Glu Glu Ala Leu Glu Glu Leu Met Arg Ala Lys Ala Arg Gly Val Asp
                245                 250                 255

Ala Leu Ala Glu Thr Cys Thr Gln Tyr Leu Tyr Leu Thr Lys Asp Asp
            260                 265                 270

Leu Asp Arg Pro Gly Phe Glu Gly Ala Lys Phe Val Phe Thr Pro Pro
        275                 280                 285

Pro Arg Glu Val Lys Asp Gln Glu Ile Leu Trp Glu Ala Leu Ala Asn
    290                 295                 300
```

-continued

```
Arg Val Phe Glu Thr Val Ser Ser Asp His Cys Ser Trp Leu Tyr Lys
305                 310                 315                 320

Gly His Lys Asp Glu Gly Leu His Asp Phe Arg Leu Ile Pro Asn Gly
                325                 330                 335

Ala Pro Gly Val Glu Glu Arg Met Met Met Val Tyr Gln Gly Val Asn
            340                 345                 350

Gln Gly Arg Ile Ser Leu Thr Gln Phe Val Asp Leu Val Ala Thr Arg
        355                 360                 365

Pro Ala Gln Val Phe Gly Met Phe Pro Gln Lys Gly Thr Ile Ala Val
    370                 375                 380

Gly Ser Asp Ala Asp Leu Val Ile Trp Asp Pro Glu Ala Thr Met Thr
385                 390                 395                 400

Ile Thr Gln Ser Ala Met Asn Asn Ala Met Asp Tyr Ser Thr Tyr Glu
                405                 410                 415

Gly Gln Ala Val Lys Gly Met Pro Thr Thr Val Val Leu Arg Gly Lys
            420                 425                 430

Val Ile Val Glu Asp Arg Asn Tyr Val Gly Thr Pro Gly Glu Gly Arg
        435                 440                 445

Phe Leu Arg Arg Glu Arg Tyr Ala Arg Ser Pro Lys Leu Ala
    450                 455                 460
```

<210> SEQ ID NO 3
<211> LENGTH: 924
<212> TYPE: DNA
<213> ORGANISM: Pasteurella pneumotropica
<220> FEATURE:
<221> NAME/KEY: CDS
<222> LOCATION: (1)..(921)
<223> OTHER INFORMATION:

<400> SEQUENCE: 3

```
atg agc agg aag atg att ctc gcc gtt ggc cag cag ggg ccg atc cag      48
Met Ser Arg Lys Met Ile Leu Ala Val Gly Gln Gln Gly Pro Ile Gln
1               5                   10                  15 cgc gcc gat acg cgc gag cag gtc gtc gcg cgg ctg atc gag atg ctg      96
Arg Ala Asp Thr Arg Glu Gln Val Val Ala Arg Leu Ile Glu Met Leu
                20                  25                  30 aag gaa gcg aag gcg cgc aac gcc gat ttc gtc gtc ttc ccc gag ctc     144
Lys Glu Ala Lys Ala Arg Asn Ala Asp Phe Val Val Phe Pro Glu Leu
            35                  40                  45 gcc ctg acc acc ttc ttc ccg cgc tgg tac ttc acc gac gag gcg gag     192
Ala Leu Thr Thr Phe Phe Pro Arg Trp Tyr Phe Thr Asp Glu Ala Glu
        50                  55                  60 ctc gac ttc ttc tac gaa acg gag atg ccg ggg ccg gca acg cgc ccg     240
Leu Asp Phe Phe Tyr Glu Thr Glu Met Pro Gly Pro Ala Thr Arg Pro
65                  70                  75                  80 ctg ttc gag aag gcg acc gag ctc ggc atc ggc ttc acc atc tcc ttc     288
Leu Phe Glu Lys Ala Thr Glu Leu Gly Ile Gly Phe Thr Ile Ser Phe
                85                  90                  95 gcc gag ctg gtg atg gag ggg acg acc aag cgg cgc ttc aac acc tcg     336
Ala Glu Leu Val Met Glu Gly Thr Thr Lys Arg Arg Phe Asn Thr Ser
            100                 105                 110 ctg gcg atc gac aag tcc ggc cgg gtc gcc ggc aag tac cgc aag atc     384
Leu Ala Ile Asp Lys Ser Gly Arg Val Ala Gly Lys Tyr Arg Lys Ile
        115                 120                 125 cat ctc ccc ggc cac aag gaa tac gag gcc tac cgg ccg ttc cag cac     432
His Leu Pro Gly His Lys Glu Tyr Glu Ala Tyr Arg Pro Phe Gln His
    130                 135                 140 ctc gag aag cgc tat ttc gag agc ggc gac ctc ggc ttc cag gtc aac     480
Leu Glu Lys Arg Tyr Phe Glu Ser Gly Asp Leu Gly Phe Gln Val Asn
```

```
                                    -continued

Leu Glu Lys Arg Tyr Phe Glu Ser Gly Asp Leu Gly Phe Gln Val Asn
145                 150                 155                 160 gac gtc gac ggc gcc aag ctc ggc atg ttc atc tgc aac gac cgc cgc      528
Asp Val Asp Gly Ala Lys Leu Gly Met Phe Ile Cys Asn Asp Arg Arg
                165                 170                 175 tgg ccg gag acc tgg cgc gtc atg ggc ctc aag ggc gcc gag atc atc      576
Trp Pro Glu Thr Trp Arg Val Met Gly Leu Lys Gly Ala Glu Ile Ile
            180                 185                 190 tgc ggc ggc tac aac acg ccg ctg cac aac ccg ccc gtg ccg cag cat      624
Cys Gly Gly Tyr Asn Thr Pro Leu His Asn Pro Pro Val Pro Gln His
        195                 200                 205 gac cag ctg agc tcg ttc cac cac ctg ctg tcg atg cag gcc ggg gcg      672
Asp Gln Leu Ser Ser Phe His His Leu Leu Ser Met Gln Ala Gly Ala
    210                 215                 220 tac cag aac ggc gcc tgg gcg gcg gct gcc ggc aag gtc ggc atc gag      720
Tyr Gln Asn Gly Ala Trp Ala Ala Ala Ala Gly Lys Val Gly Ile Glu
225                 230                 235                 240 gaa ggc tgc atg ctg ctc ggc cat tcc tgc atc gtg gcg ccg aca ggc      768
Glu Gly Cys Met Leu Leu Gly His Ser Cys Ile Val Ala Pro Thr Gly
                245                 250                 255 gag ctc gtc gcc atg acc aac acg ctc gag gac gag gtg atc acc gcc      816
Glu Leu Val Ala Met Thr Asn Thr Leu Glu Asp Glu Val Ile Thr Ala
            260                 265                 270 gcc gtc gac ctc gat cgc tgc cgc gag atc cgc gag aac atc ttc aac      864
Ala Val Asp Leu Asp Arg Cys Arg Glu Ile Arg Glu Asn Ile Phe Asn
        275                 280                 285 ttc gcc ctg cac cgc gaa ccg aag aac tac gcg atc atc gcg gaa gaa      912
Phe Ala Leu His Arg Glu Pro Lys Asn Tyr Ala Ile Ile Ala Glu Glu
    290                 295                 300 cag gtc cgc tag                                                      924
Gln Val Arg
305

<210> SEQ ID NO 4
<211> LENGTH: 307
<212> TYPE: PRT
<213> ORGANISM: Pasteurella pneumotropica

<400> SEQUENCE: 4

Met Ser Arg Lys Met Ile Leu Ala Val Gly Gln Gln Gly Pro Ile Gln
1               5                   10                  15

Arg Ala Asp Thr Arg Glu Gln Val Val Ala Arg Leu Ile Glu Met Leu
            20                  25                  30

Lys Glu Ala Lys Ala Arg Asn Ala Asp Phe Val Val Phe Pro Glu Leu
        35                  40                  45

Ala Leu Thr Thr Phe Phe Pro Arg Trp Tyr Phe Thr Asp Glu Ala Glu
    50                  55                  60

Leu Asp Phe Phe Tyr Glu Thr Glu Met Pro Gly Pro Ala Thr Arg Pro
65                  70                  75                  80

Leu Phe Glu Lys Ala Thr Glu Leu Gly Ile Gly Phe Thr Ile Ser Phe
                85                  90                  95

Ala Glu Leu Val Met Glu Gly Thr Thr Lys Arg Arg Phe Asn Thr Ser
            100                 105                 110

Leu Ala Ile Asp Lys Ser Gly Arg Val Ala Gly Lys Tyr Arg Lys Ile
        115                 120                 125

His Leu Pro Gly His Lys Glu Tyr Glu Ala Tyr Arg Pro Phe Gln His
    130                 135                 140

Leu Glu Lys Arg Tyr Phe Glu Ser Gly Asp Leu Gly Phe Gln Val Asn
```

-continued

```
            145                 150                 155                 160
Asp Val Asp Gly Ala Lys Leu Gly Met Phe Ile Cys Asn Asp Arg Arg
                165                 170                 175
Trp Pro Glu Thr Trp Arg Val Met Gly Leu Lys Gly Ala Glu Ile Ile
            180                 185                 190
Cys Gly Gly Tyr Asn Thr Pro Leu His Asn Pro Val Pro Gln His
        195                 200                 205
Asp Gln Leu Ser Ser Phe His His Leu Leu Ser Met Gln Ala Gly Ala
    210                 215                 220
Tyr Gln Asn Gly Ala Trp Ala Ala Ala Gly Lys Val Gly Ile Glu
225                 230                 235                 240
Glu Gly Cys Met Leu Leu Gly His Ser Cys Ile Val Ala Pro Thr Gly
                245                 250                 255
Glu Leu Val Ala Met Thr Asn Thr Leu Glu Asp Glu Val Ile Thr Ala
            260                 265                 270
Ala Val Asp Leu Asp Arg Cys Arg Glu Ile Arg Glu Asn Ile Phe Asn
        275                 280                 285
Phe Ala Leu His Arg Glu Pro Lys Asn Tyr Ala Ile Ile Ala Glu Glu
    290                 295                 300
Gln Val Arg
305

<210> SEQ ID NO 5
<211> LENGTH: 2833
<212> TYPE: DNA
<213> ORGANISM: Pasteurella pneumotropica

<400> SEQUENCE: 5
gatcctcgcc tatctcggcc tcggccatgt cggaaacgaa ctggcccgca acctgccgca      60
cggctatctg cgcacgctcg gcatcgccat cgccatggcg gcgaacccgc gcatcctgct     120
gctcgacgaa cccttcgccg gcatgaaccc ggaagagacg gaccgcgccg tcgaaatggt     180
ggagggaatc cgccgccgcg gcatcaccgt cctgctcgtc gagcacgaca tgcgcgccgt     240
gatgcggatc agcgaccgga tcgtcgtcat cagcttcggc tcgaagattg cagagggaac     300
cccggcggag atccgggaca acccaaccgt catcgaggcc tatctcggcc aggacgacga     360
gacgatcgga cactgacatg gcgggaagca gcatgcgata tttcgaggca gcggcctga     420
ccgtcaacta taaccgcgtc gcgccatcg ccgatgtcgg cctcgccttc gacgagggca     480
aggttgcctc gctgatcggc gccaatggcg cgggaaagag cacgacgctg cgggcgatca     540
ccggcctcgt cccgctcgcc ggcggcgaaa tctggttcga cggcgcccgc atcgaccgcc     600
tcccggcgcc gcgccgggtc gagatcgcg tcgccatggt gccggagggc cggcgcgtct     660
tcccgcagat gagcgtgcgc gacaacctgc tgatgggcgc ctatgcgcgc aaggatcgcg     720
gcgccatcgc cagcgacctc gaacggatcc tgacccgctt cccccgcctc aaggaacgcc     780
tgcgccaggg cgccggcacg ctgtcgggcg gcgagcagga gatgctcgtc atcggccgcg     840
ccctgatgtc gaagccgaag ctgctgctgc tcgacgaacc ctcgctcggc ctggcgccgc     900
tggtcgtgcg cgacatcgcg aggctgatca tcgaggtcaa tcgcgacgag ggcatgagca     960
tcgtgctcgt cgaacagaac tcgcggatgg cgctgcgcgt cagccagtac ggctacgtgc    1020
tggagaccgg ccgcatcgcg ctcgaaggcc cttcggacgc actgctgaac gaccccaagg    1080
tcaaggaact ctatctcggc ggctaaggcc gccctccatc gaaccatcga ggattttgga    1140
atgagcagga agatgattct cgccgttggc cagcaggggc cgatccagcg cgccgatacg    1200
```

```
cgcgagcagg tcgtcgcgcg gctgatcgag atgctgaagg aagcgaaggc gcgcaacgcc      1260
gatttcgtcg tcttccccga gctcgccctg accaccttct tcccgcgctg gtacttcacc      1320
gacgaggcgg agctcgactt cttctacgaa acggagatgc cggggccggc aacgcgcccg      1380
ctgttcgaga aggcgaccga gctcggcatc ggcttcacca tctccttcgc cgagctggtg      1440
atggagggga cgaccaagcg gcgcttcaac acctcgctgg cgatcgacaa gtccggccgg      1500
gtcgccggca agtaccgcaa gatccatctc cccggccaca aggaatacga ggcctaccgg      1560
ccgttccagc acctcgagaa cgcgctattt cgagagcggcg acctcggctt ccaggtcaac      1620
gacgtcgacg gcgccaagct cggcatgttc atctgcaacg accgccgctg gccggagacc      1680
tggcgcgtca tgggcctcaa gggcgccgag atcatctgcg gcggctacaa cacgccgctg      1740
cacaacccgc ccgtgccgca gcatgaccag ctgagctcgt tccaccacct gctgtcgatg      1800
caggccgggg cgtaccagaa cggcgcctgg cggcggcctg ccggcaaggt cggcatcgag      1860
gaaggctgca tgctgctcgg ccattcctgc atcgtggcgc cgacaggcga gctcgtcgcc      1920
atgaccaaca cgctcgagga cgaggtgatc accgccgccg tcgacctcga tcgctgccgc      1980
gagatccgcg agaacatctt caacttcgcc ctgcaccgcg aaccgaagaa ctacgcgatc      2040
atcgcggaag aacaggtccg ctagcgggcg tcgccgggct cggcggccgg ggtgatcggc      2100
gtgaccaccg cctggcatct ggccgaagcc ggccgccagg taacgatttt cgtccccgc      2160
cgccgggcgc ggatctcgcc gacgtcgacc tcgccccctt tgcgcccgt tagatcgaac      2220
ccgaggaacc ccgatgaaga tcaaggtgat caacccgaac accacctggt ccatgaccga      2280
gaagatcggc gaggcggcgc gacgcgtggc ggcgcccggc accgagatcg tcgccgtgtc      2340
gccggcaatg ggcccggtct cgatcgaggg cttctatgac gaggccttcg ccgccatcgg      2400
cgtcatcgac gaagtgcgga agggcgagga agagggctgc gacggctatg tcatcgcctg      2460
cttcggcgat ccgggcctgc tggcggcgcg cgagatcgcg cgcggaccgg tcgtcggcat      2520
cgccgaggcg gccatgcatg cggcgagcct gatcggcaac ggcttcacca tcgtctcgat      2580
gctggagcgg acgcgggcga cgatggaaca cctcgtgcac gcctatggca tgagccacaa      2640
gtgccgcaac atccgcatga ccgacctgcc ggtgctggaa ctggaaaagg aaggctcgaa      2700
cgcgcaggcg atcatcatcg aggaatgccg ccgcgcgctg gaagaggacc attccgacgc      2760
ggtgctgctc ggctgcggcg gcatgtcgga cctgatggcg ctcatcaccc gcgagatcgg      2820
cgcgccggcg atc                                                         2833

<210> SEQ ID NO 6
<211> LENGTH: 2263
<212> TYPE: DNA
<213> ORGANISM: Pasteurella pneumotropica

<400> SEQUENCE: 6
gatcctgtcg tgggaagggg gaaggaagcg ggcctggccc gcgacgtcct gcgccgcctt       60
cccgcgctcc gggttgggcc tgcgcccctgt cctctcgtcc gaagtcggcc cggcatggac      120
cgattcctgc atcccggccc gcgcggggcc ggcccgcctg tgaaaccccta ttggagactg      180
tcgatggatc tcatcgtcaa gaacggaacg atcgtcaccg ccgccggcat ttcgcgcgcg      240
gatctcggcg tcagggacgg caagatcgtc cagatcggcg cgatctcgg cgaggcggcg      300
cgcacgatcg acgcgaccgg ccgctatgtc atgccgggcg cgtcgacgt ccacacccat      360
atcgactcca acaacatgga gacgaagtcg gcggacgatt tccggaccgg cacgatcgcg      420
```

```
gcggcctgtg gcggcacgac gacgatcgtc gatttctgcg cccaggaccg gggcggcacg      480
ctcgccgagg cgatcgccaa atgggacggg cgggcggccg gcaaggcggc gatcgactac      540
ggctaccatg tcatcgtgct cgacatgaat cccggcgtgt cgaggagtt gctgacgctg       600 ccggagcgtg gcattccctc cttcaaggtg ttcatggcct atcgcggcat gaacatgatc      660
gacgacgtca ccctgctgaa gacgctggag caggccaagc gctcggggc gctggtcatg       720 gtccatgccg agaacggtga tgcggcggat ttcctgcgcg acaagttcgt cgccgagggc      780
aagacctcgc cgaaataccg cgcgctcagc cggccgccgc gggtcgaggc cgaggcgacc      840
gcgcgcgcca tcgcgatggc cgagatcgtc ggcacctcga tctacatcgt gcacctgacc      900
tgcgaggagg cgctggagga actgatgcgc gccaaggcgc gcggcgtcga cgcgctggcc      960
gagacctgca cgcagtatct ctacctgacc aaggacgacc tcgaccggcc gggcttcgag     1020
ggggcgaagt tcgtcttcac gccgccgccg cgcgaggtca aggaccagga atcctctgg      1080 gaggcgctgg ccaaccgcgt gttcgagacg gtgtcgtccg atcactgctc ctggctctac     1140
aagggccaca aggatgaggg cctgcacgat ttccggctga tcccgaacgg ggcgcccggc     1200
gtcgaggagc ggatgatgat ggtctaccag ggcgtcaacc agggccgcat ctcgctgacc     1260
cagttcgtcg acctggtggc gacgcggccg gcgcaggtgt tcggcatgtt cccgcagaag     1320
ggcaccatcg ccgtcggctc cgacgccgac ctcgtcatct gggacccgga ggcgacgatg     1380
acgatcaccc agtcggcgat gaacaacgcg atggactact cgacctatga gggccaggcc     1440
gtcaagggaa tgcccacgac ggtggtgctg cgcggcaagg tcatcgtcga ggatcgcaac     1500
tatgtcggca cgcccggcga agggcgtttc ctgcggcgcg agcgctacgc gcgttccccg     1560
aagctcgcct gaggcagcgg cgcccccctgg aatcgtagag gcgcccgccc cgatcgaatc    1620
gtggcgggcg cggcattcgc cgcgtcagag gatgcgtcc gggccggcgc cgcagacgat      1680
cgcgcagacc ttctctgccg gcccgatcac gacccgttgc ttcatcaaag cggcgatcga     1740
ggcggcgccg ctcaggtcgg cggccaggcc catctcgaac cagagccatt tcgcggcttc     1800
ggccatttcg tcgtcgtcga ccagcacgat ctcgtcgaca ttctgccgga cgatctcgaa     1860
gatcctcgga tcggtatgcg agcacgacat cgtcgcgacc tttgtcgtcg acacgccgat     1920
gtcgacattc cggcccgctt cgagcgagcg caacagggtc ggagagcccg tcgccgcgat     1980
gccgacgacg cgcacatgcg gcgccagcgc cttgatcgcc gtcgacacgc cgctgatcag     2040
tccgccgccg ccgatggcga cgagcaccgt gtcgagatcg gcgaattgct cgaggatctc     2100
gagcccgacg gtgccctgtc cggcgacgac ataggggtcg gcgaagggt ggaaataggc      2160 ggcgcctgtt tcggcgacga aggccatcgc ggctgcgttc gcctcctgcc aggcatcgcc     2220
gatgatcacc gtttcggcgc cccattcctg gagcttgctg atc                       2263
```

<210> SEQ ID NO 7
<211> LENGTH: 35
<212> TYPE: DNA
<213> ORGANISM: ARTIFICIAL SEQUENCE
<220> FEATURE:
<223> OTHER INFORMATION: SYNTHETIC DNA

<400> SEQUENCE: 7

```
cgctctagag ggagactgac gatggatctc atcgt                                 35
```

<210> SEQ ID NO 8
<211> LENGTH: 27
<212> TYPE: DNA
<213> ORGANISM: ARTIFICIAL SEQUENCE

```
<220> FEATURE:
<223> OTHER INFORMATION: SYNTHETIC DNA

<400> SEQUENCE: 8
cgcaagcttc ctctgacgcg gcgaatg                                              27

<210> SEQ ID NO 9
<211> LENGTH: 33
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
cgcgaattcc atcgaaccag ggaggatttt gga                                       33

<210> SEQ ID NO 10
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
cgctctagac gcccgctagc ggacctgtt                                            29
```

DNA FOR ENCODING D-HYDANTOIN HYDROLASES, DNA FOR ENCODING N-CARBAMYL-D-AMINO ACID HYDROLASES, RECOMBINANT DNA CONTAINING THE GENES, CELLS TRANSFORMED WITH THE RECOMBINANT DNA, METHODS FOR PRODUCING PROTEINS UTILIZING THE TRANSFORMED CELLS AND METHODS FOR PRODUCING D-AMINO ACIDS

FIELD OF THE INVENTION

The present invention relates to a DNA for encoding D-hydantoin hydrolase ("D-hydantoinase") which is utilized preferably for producing D-amino acid, a DNA for encoding N-carbamyl-D-amino acid hydrolase ("D-carbamylase"), a recombinant DNA containing the gene, a cell transformed with the recombinant DNA, a methods for producing a protein using the transformed cell and producing D-amino acid.

BACKGROUND OF THE INVENTION

In a known method for producing amino acid using an enzyme, a 5-substituted hydantoin compound synthesized chemically at a low cost is employed as a starting material and is decomposed asymmetrically into optically active amino acids. A method for producing optically active amino acid from such a 5-substituted hydantoin compound is important for producing pharmaceuticals, chemical industrial products, food additives and the like.

In a method for producing optically active amino acid from such a 5-substituted hydantoin compound, the following enzymes (1) and (2) are required:

(1) An enzyme which catalyzes an N-carbamylamino acid producing reaction via an action on a 5-hydantoin compound to hydrolyze this compound: hydantoin hydrolase (hydantoinase).

(2) An enzyme which catalyzes an optically active amino acid producing reaction via an action on a resultant N-carbamylamino acid to hydrolyze this compound, N-carbamylamino acid hydrolase (carbamylase).

For producing optically active amino acid from a 5-substituted hydantoin compound describe above, an enzyme which is optically selective for at least one of (1) hydantoinase and (2) carbamylase may be employed, and known methods employ a microbial enzyme system or a microbial enzyme system combined with a chemical reaction system.

Among such known methods, a known method for producing D-amino acid from a 5-substituted hydantoin compound using a D-amino acid producing microorganism or a material containing an enzyme produced by the microorganism employs a *Pseudomonas* microorganism (Japanese Patent Application Publication No. 56-003034) or an *Agrobacterium* microorganism (Japanese Patent Application Laid-open No. 019696). Such a D-amino acid producing microorganism frequently has a hydantoinase activity specific generally to a 5-substituted hydantoin in a D form, and when using a DL-5-substituted hydantoin (5-benzylhydatoin as an example here) as a starting material, the D form is hydrolyzed exclusively to form an N-carbamyl-D-amino acid, which is then hydrolyzed by a D-carbamylase which acts exclusively on the D form, resulting in only an amino acid in the D form (D-phenylalanine as an example here), as shown in the following scheme.

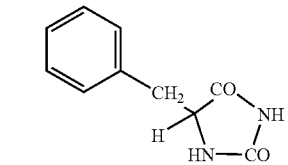

DL-5-SUBSTITUTED HYDANTOIN

D-HYDANTOINASE

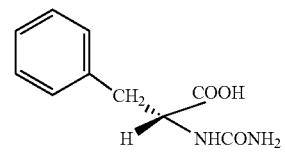

N-CARBAMYL-D-AMINO ACID

D-CARBAMYLASE

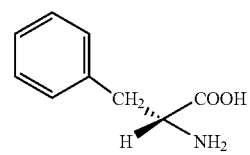

D-AMINO ACID

SUMMARY OF THE INVENTION

Thus, a production of an optically active amino acid from a 5-substituted hydantoin compound using a cultured cell of a D-amino acid producing microorganism involves here a problem resulting from the need of a derivative such as a hydantoin derivative for the purpose of increasing the production of an enzyme required for the reaction, or the need of a massive amount of the cultured cell.

On the other hand, for the purpose of an efficient production of an optically active amino acid, it is preferable that a D-hydantoinase gene and a D-carbamylase gene are isolated and imparted with an increased gene amplification, transcription and translation to obtain a recombinant whose ability of producing such an enzyme is enhanced, which is then employed in the production. However, a conventional method is problematically time consuming in effecting a reaction, and the reaction allows an N-carbamyl-D-amino acid to be formed as a by-product.

It is an object of the present invention to isolate a D-hydantoinase gene and a D-carbamylase gene from a microorganism having an ability of converting a 5-substituted hydantoin compound to a D-amino acid whereby elucidating the amino acid sequence and the base sequence of an encoding gene and to construct a recombinant whose production of the enzyme is enhanced whereby providing a method for producing the D-amino acid efficiently from the 5-substituted hydantoin.

The present inventors made an effort for solving the problems described above, and were finally successful in isolating a D-hydantoinase gene and a D-carbamylase gene from a microorganism having an ability of converting a 5-substituted hydantoin compound into a D-amino acid, whereby establishing the present invention.

The DNA according to one aspect of the present invention has a base sequence represented by (a) or (b) and that encodes a protein having D-hydantoinase activity, wherein
(a) is the base sequence represented by Seq. ID No. 1 in the Sequence Listing; and
(b) is a base sequence hybridizing with a complementary base sequence of the base sequence represented by Seq. ID No. 1 in the Sequence Listing under a stringent condition for encoding.

The DNA according to another aspect of the present invention has an amino acid sequence represented by (c) or (d) and that encodes a protein having D-hydantoinase activity, wherein
(c) is the amino acid sequence represented by Seq. ID No. 2 in the Sequence Listing;
(d) is an amino acid sequence resulting from the substitution, deletion, insertion, addition or inversion of one or several amino acid residues in the amino acid sequence represented by Seq. ID No. 2 in the Sequence Listing.

The recombinant DNA according to a third aspect of the present invention results from a connection of a DNA according to the first aspect with a vector DNA.

The recombinant DNA according to a fourth aspect of the present invention results from a connection of a DNA according to the second aspect with a vector DNA.

The cell according to a fifth aspect is transformed with a recombinant DNA according to the third aspect.

The cell according to a sixth aspect is transformed with a recombinant DNA according to the fourth aspect.

The method for producing a protein having D-hydantoinase activity according to a seventh aspect comprises incubating a cell in a culture medium, and allowing a protein having D-hydantoinase activity to be accumulated in one or both of the culture medium and the cell. The cell being the cell according to the fifth aspect.

The method for producing a protein having D-hydantoinase activity according to an eighth aspect comprises incubating a cell in a culture medium, and allowing a protein having D-hydantoinase activity to be accumulated in one or both of the culture medium and the cell. The cell being the cell according to the sixth aspect.

The protein according to a ninth aspect of the present invention has an amino acid sequence represented by (a) or (b) and having D-hydantoinase activity, wherein
(a) is the amino acid sequence represented by Seq. ID No. 2 in the Sequence Listing; and
(b) is an amino acid sequence resulting from the substitution, deletion, insertion, addition or inversion of one or several amino acid residues in the amino acid sequence represented by Seq. ID No. 2 in the Sequence Listing.

The method for producing N-carbamyl-D-amino acid according to a tenth aspect of the present invention comprises producing a protein having D-hydantoinase activity by the method according to the seventh aspect, and producing N-carbamyl-D-amino acid by making the protein having D-hydantoinase activity react with a 5-substituted hydantoin. The cell being the cell according to the fifth aspect.

The method for producing N-carbamyl-D-amino acid according to an eleventh aspect of the present invention comprises producing a protein having D-hydantoinase activity by the method according to the eighth aspect, and producing N-carbamyl-D-amino acid by making the protein having D-hydantoinase activity react with a 5-substituted hydantoin. The cell being the cell according to the sixth aspect.

The method for producing D-amino acid according to a twelfth aspect of the present invention comprises producing a protein having D-hydantoinase activity by the method according to the seventh aspect, and producing D amino acid by making the protein having D-hydantoinase activity and an enzyme hydrolyzing an N-carbamyl-D-amino acid or a material containing the enzyme react with a 5-substituted hydantoin. The cell being the cell according to the fifth aspect.

The method for producing D-amino acid according to a thirteenth aspect of the present invention comprises producing a protein having D-hydantoinase activity by the method according to the eighth aspect, and producing D-amino acid by making the protein having D-hydantoinase activity and an enzyme hydrolyzing an N-carbamyl-D-amino acid or a material containing the enzyme react with a 5-substituted hydantoin. The cell being the cell according to the sixth aspect.

The DNA according to a fourteenth aspect of the present invention has a base sequence represented by (a) or (b) and that encodes a protein having D-carbamylase activity, wherein
(a) is the base sequence represented by Seq. ID No. 3 in the Sequence Listing; and
(b) is a base sequence hybridizing with a complementary base sequence of the base sequence represented by Seq. ID No. 3 in the Sequence Listing under a stringent condition.

The DNA according to a fifteenth aspect of the present invention has an amino acid sequence represented by (c) or (d) and that encodes a protein having D-carbamylase activity, wherein
(c) is the amino acid sequence represented by Seq. ID No. 4 in the Sequence Listing; and
(b) is an amino acid sequence resulting from the substitution, deletion, insertion, addition or inversion of one or several amino acid residues in the amino acid sequence represented by Seq. ID No. 4 in the Sequence Listing.

The recombinant DNA according to a sixteenth aspect of the present invention results from a connection of the DNA according to the fourteenth aspect with a vector DNA.

The recombinant DNA according to a seventeenth aspect of the present invention results from a connection of the DNA according to the fifteenth aspect with a vector DNA.

The cell according to an eighteenth aspect of the present invention is transformed with a recombinant DNA according to the sixteenth aspect.

The cell according to a nineteenth aspect of the present invention is transformed with a recombinant DNA according to the seventeenth aspect.

The method for producing a protein having D-carbamylase activity according to a twentieth aspect of the present invention comprises incubating a cell in a culture medium, and allowing a protein having D-carbamylase activity to be accumulated in one or both of the culture medium and the cell. The cell being the cell according to the eighteenth aspect.

The method for producing a protein having D-carbamylase activity according to a twenty-first aspect of the present invention comprises incubating a cell in a culture medium, and allowing a protein having D-carbamylase activity to be accumulated in one or both of the culture medium and the cell. The cell being the cell according to the nineteenth aspect.

The protein according to a twenty-second aspect of the present invention has an amino acid sequence represented by (a) or (b) and having D-carbamylase activity, wherein
(a) is the amino acid sequence represented by Seq. ID No. 4 in the Sequence Listing; and
(b) is an amino acid sequence resulting from the substitution, deletion, insertion, addition or inversion of one or several amino acid residues in the amino acid sequence represented by Seq. ID No. 4 in the Sequence Listing.

The method for producing D-amino acid according to a twenty-third aspect of the present invention comprises producing a protein having D-carbamylase activity by the method according to the twentieth aspect, and producing D-amino acid by making the protein having D-carbamylase activity react with an N-carbamylamino acid. The cell being the cell according to the eighteenth aspect.

The method for producing D-amino acid according to a twenty-fourth aspect of the present invention comprises producing a protein having D-carbamylase activity by the method according to the twenty-first aspect, and producing D-amino acid by making the protein having D-carbamylase activity react with an N-carbamylamino acid. The cell being the cell according to the nineteenth aspect.

The method for producing D-amino acid according to a twenty-fifth aspect of the present invention comprises producing a protein having D-carbamylase activity by the method according to the twentieth aspect, and producing D-amino acid by making the protein having D-carbamylase activity and an enzyme hydrolyzing a 5-substituted hydantoin or a material containing the enzyme react with a 5-substituted hydantoin. The cell being the cell according to the eighteenth aspect.

The method for producing D-amino acid according to a twenty-sixth aspect of the present invention comprises producing a protein having D-carbamylase activity by the method according to the twenty-first aspect, and producing D-amino acid by making the protein having D-carbamylase activity and an enzyme hydrolyzing a 5-substituted hydantoin or a material containing the enzyme react with a 5-substituted hydantoin. The cell being the cell according to the nineteenth aspect.

The method for producing D-amino acid according to a twenty-seventh aspect of the present invention comprises producing a protein having D-hydantoinase activity by the method according to the seventh aspect, the cell being the cell according to the fifth aspect, producing a protein having D-carbamylase activity by the method according to the twentieth aspect, the cell being the cell according to the eighteenth aspect, and producing D-amino acid by making the protein having D-hydantoinase activity and the protein having D-carbamylase activity react with a 5-substituted hydantoin.

The method for producing D-amino acid according to a twenty-eighth aspect of the present invention comprises producing a protein having D-hydantoinase activity by the method according to the seventh aspect, the cell being the cell according to the fifth aspect, producing a protein having D-carbamylase activity by the method according to the twenty-first aspect, the cell being the cell according to the nineteenth aspect, and producing D-amino acid by making the protein having D-hydantoinase activity and the protein having D-carbamylase activity react with a 5-substituted hydantoin.

The method for producing D-amino acid according to a twenty-ninth aspect of the present invention comprises producing a protein having D-hydantoinase activity by the method according to the eighth aspect, the cell being the cell according to the sixth aspect, producing a protein having D-carbamylase activity by the method according to the twentieth aspect, the cell being the cell according to the eighteenth aspect, and producing D-amino acid by making the protein having D-hydantoinase activity and the protein having D-carbamylase activity react with a 5-substituted hydantoin.

The method for producing D-amino acid according to a thirtieth aspect of the present invention comprises producing a protein having D-hydantoinase activity by the method according to the eighth aspect, the cell being the cell according to the sixth aspect, producing a protein having D-carbamylase activity by the method according to the twenty-first aspect, the cell being the cell according to the nineteenth aspect, and producing D-amino acid by making the protein having D-hydantoinase activity and the protein having D-carbamylase activity react with a 5-substituted hydantoin.

Other objects and features of this invention will become apparent from the following description with reference to the accompanying drawings.

DETAILED DESCRIPTIONS

Figure 1:
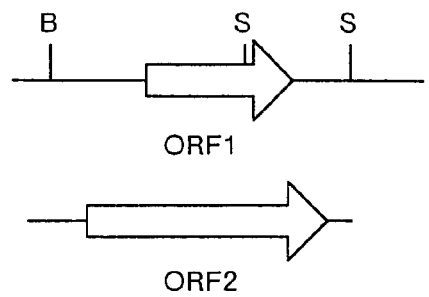
FIG. 1 is a schematic view of the group of the genes encoding the D-hydantoinase and D-carbamylase of strains AJ11221.

Embodiments of the present invention are described below in the order:
[I] DNA for encoding protein having D-hydantoinase activity and protein having D-carbamylase activity,
[II] Method for producing protein having D-hydantoinase activity and protein having D-carbamylase activity, and
[III] Method for producing D-amino acid.

In the following descriptions, a protein having D-hydantoinase activity is sometimes simply referred to as a D-hydantoinase. Moreover, a protein having D-carbamylase activity is sometimes simply referred to as a D-carbamylase.

[I] DNA for encoding D-hydantoinase and D-carbamylase:

DNA for encoding D-hydantoinase and D-carbamylase according to the invention is obtained by isolating it from a chromosomal DNA of *Pasteurella pneumotropica* strain AJ11221 (FERM-P4348) described in Japanese Patent Application Publication No. 56-015878. *Pasteurella pneumotropica* strain AJ11221 (FERM-P4348) was a microorganism which had initially been deposited under the name of *Moraxella nonliquefaciens* in National Institute of Bioscience and Human-Technology, Ministry of Economy, Trade and Industry, METI, but was subsequently re-identified to be classified in *Pasteurella pneumotropica*. Currently, *Pasteurella pneumotropica* has been deposited as FERM P-4348 with the Research Institute of Bioscience and Human-technology, AIST, MITY, JAPAN, on Dec. 20, 1977. Later, on May 30, 2002, the same strain has been deposited as FERM BP-8064 based on Budapest convention in the International Patent Organism Depository (IPOD), National Institute of Advanced Industrial Science and Technology (AIST), Japan (Tsukuba City, Higashi 1-1-1, Ibaraki Prefecture, Japan).

The microorganism described above was subjected to physiological and physical tests in accordance with Bergey's Manual of Determinative Bacteriology, Vol.1 (9th edition, 1994, Williams & Wilkins) which is a text for characterizing microorganisms, and the following results were obtained.

Results of re-identification of *Pasteurella pneumotropica* strain AJ11221

| Gram staining | Negative |
|---|---|
| Cell morphology | Spherical baccilus |
| Mobility | None |
| Nitrate reduction | + |
| Indole production | − |
| Glucose acidificaiton | − |
| Arginine dihydraze | − |
| Urease | + |
| Esculin hydrolysis | − |
| Gelatin hydrolysis | − |
| β-Galactosidase | + |
| Catalase | + |
| Oxidase | + |
| Substrate catabolyzing ability | |
| Glucose | − |
| L-Arabinose | − |
| D-Mannose | − |
| D-Mannitol | − |
| N-Acetyl-D-glucosamine | − |
| Maltose | + |
| Potassium gluconate | − |
| n-Capric acid | − |
| Adipic acid | − |
| dl-Malic acid | − |
| Sodium citrate | − |
| Phenyl acetate | − |

Based on the bacteriological characteristics described above, AJ11221 microorganism was identified as *Pasteurella pneumotropica*.

The present inventors were successful in obtaining a D-hydantoinase gene and D-carbamylase gene as being isolated from a gene library prepared using chromosomal DNAs of the AJ11221 microorganism described above. It is presumed that these genes are located at separated locations on the chromosome.

The method of a PCR employed for isolating the genes are described for example in White, T. J. et al., Trends Genet. Vol.5, p. 185, 1989. The methods for preparing a chromosomal DNA and for isolating an intended DNA molecule from a gene library using a DNA molecule as a probe are described for example in Molecular Cloning, 2nd edition, Cold Spring Harbor press (1989).

A method for sequencing a DNA for encoding the isolated D-hydantoinase or D-carbamylase is described for example in A Practical Guide to Molecular Cloning, John Wiley & Sons, Inc. (1985). It is also possible to determine a base sequence using a DNA sequencer manufactured by Applied Biosystems.

In the Sequence Listing attached hereto, the base sequence of the DNA for encoding the D-hydantoinase derived from the AJ11199 microorganism characterized by the method described above is represented by Seq. ID No. 1, while the DNA for encoding the D-carbamylase is represented by Seq. ID No. 3.

Each of these DNAs encodes a protein involved in the production of a D-amino acid.

In the Sequence Listing, Sequence ID No. 2 represents the amino acid sequence of the protein having D-hydantoinase activity encoded by the base sequence of Sequence ID No. 1, while Sequence ID No. 4 represents the amino acid sequence of the protein having D-carbamylase activity encoded by the base sequence of Sequence ID No. 3.

The protein having the D-hydantoinase activity represented by Sequence ID No. 2 in the Sequence Listing and the protein having the D-carbamylase activity represented by Sequence ID No. 4 in the Sequence Listing catalyze the reactions for forming an optically active amino acid such as D-phenylalanine from a 5-substituted hydantoin such as 5-benzylhydantoin, as shown in the following scheme.

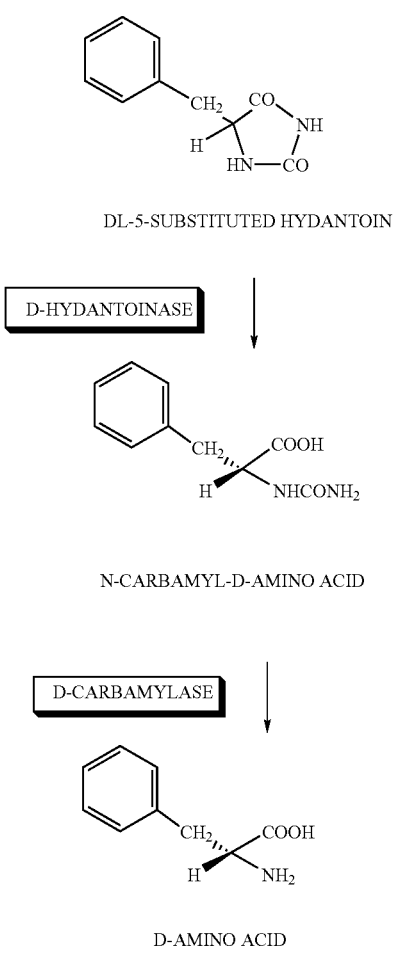

A DNA for encoding a D-hydantoinase according to the invention and a DNA for encoding a D-carbamylase are detailed below.

(1) DNA for Encoding D-hydantoinase

A D-hydantoinase gene according to the invention which has the base sequence represented by Sequence ID No. 1 in the Sequence Listing is one isolated from a chromosomal DNA of *Pasteurella pneumotropica* strain AJ11221 as described above, and has the homology of 77% (76% in amino acid sequence) to a known *Agrobacterium* microorganism-derived D-hydantoinase gene (WO96/20275).

The DNA represented by Sequence ID No. 1 in the Sequence Listing DNA is not the only DNA which encodes a D-hydantoinase according to the invention. Thus, the base sequence differs among the species and the strains of *Pasteurella* microorganisms.

The DNA according to the invention is not only a DNA for encoding the isolated D-hydantoinase but also a DNA resulting from an artificial variation of the DNA for encoding the isolated D-hydantoinase, as a matter of course, as long as a D-hydantoinase is encoded. An artificial variation method employed frequently is a site-specific variation introducing method described for example in Method in Enzymol. P154, 1987.

The DNA for encoding a protein having D-hydantoinase activity which has a base sequence capable of hybridizing under a stringent condition with a complementary base sequence of the base sequence represented by Sequence ID No. 1 in the Sequence Listing is also a DNA according to the invention. The term "stringent condition" employed here means a condition allowing a specific hybrid to be formed but not allowing a non-specific hybrid to be formed. While it is difficult to specify such a condition as definitive numerical parameters, those which may be exemplified are a condition which allows the DNAs which are highly homologous to each other, preferably have a homology of 80% or higher, more preferably a homology of 90% or higher to each other while not allowing any DNAs having a less homology and a condition of an ordinary southern hybridization washing step, i.e., a hybridization at a salt concentration corresponding to 60° C., 1×SSC, 0.1% SDS, preferably 60° C., 0.1×SSC, 0.1% SDS. The term "D-hydantoinase activity" means any activity capable of producing N-carbamyl-D-amino acid by hydrolyzing a 5-substituted hydantoin compound.

A DNA for encoding a protein which is identical substantially to the D-hydantoinase encoded by the DNA represented by Sequence ID No. 1 in the Sequence Listing is also a DNA according to the invention. Thus, the following (a) or (b) are in the scope of the present invention, where:

(a) is a DNA for encoding the amino acid sequence represented by Seq. ID No. 2 in the Sequence Listing, and
(b) is a DNA for encoding a protein having D-hydantoinase activity which has an amino acid sequence resulting from the substitution, deletion, insertion, addition or inversion of one or several amino acid residues in the amino acid sequence represented by Seq. ID No. 2 in the Sequence Listing.

For the purpose of deducing, on the basis of the amino acid sequences (a) and (b) described above, a DNA for encoding such a sequence, a DNA base sequence universal codon can be employed. The term "several" means a number which results in no substantial deterioration of the steric structure or enzymatic activity of the protein, and which is typically 2 to 50, preferably 2 to 30, more preferably 2 to 10. The term "D-hydantoinase activity" means any activity capable of producing N-carbamyl-D-amino acid by hydrolyzing a 5-substituted hydantoin compound. Nevertheless, in the case of a protein involving such a substitution, deletion, insertion, addition or inversion in the amino acid sequence represented by Seq. ID No. 2 in the Sequence Listing, it is preferred that an enzymatic activity which is at least a half of that of the protein having the amino acid sequence represented by Seq. ID No. 2 in the Sequence Listing is possessed.

(2) DNA for Encoding D-carbamylase

A DNA for encoding the D-carbamylase according to the invention is described below. The D-carbamylase of the present invention having the base sequence represented by Sequence ID No. 3 in the Sequence Listing is isolated from a chromosomal DNA of *Pasteurella pneumotropica* strain AJ11221 and has the homology of 78% (81% in amino acid sequence) to a known *Agrobacterium* microorganism-derived D-carbamylase gene (Japanese Patent Publication No. 2902112) and the homology of 67% (59% in amino acid sequence) to a known *Pseudomonas* microorganism-derived D-carbamylase gene (Japanese Patent Publication No. 2902112).

The DNA represented by Sequence ID No. 3 in the Sequence Listing DNA is not the only DNA which encodes the D-carbamylase according to the invention. Thus, the base sequence should differ among the species and the strains of *Pasteurella* microorganisms.

A DNA resulting from an artificial variation of the DNA for encoding the isolated D-hydantoinase is also DNA of the present invention as long as it encodes a D-hydantoinase. An artificial variation method employed frequently is a site-specific variation introducing method described for example in Method in Enzymol. P154, 1987.

A DNA for encoding a protein having the D-carbamylase activity which has a base sequence capable of hybridizing under a stringent condition with a complementary sequence of the base sequence represented by Sequence ID No. 3 in the Sequence Listing is also a DNA according to the invention. The term "stringent condition" employed here means a condition allowing a specific hybrid to be formed but not allowing a non-specific hybrid to be formed. While it is difficult to specify such a condition as definitive numerical parameters, those which may be exemplified are a condition which allows the DNAs which are highly homologous to each other, preferably have a homology of 80% or higher, more preferably a homology of 90% or higher to each other while not allowing any DNAs having a less homology and a condition of an ordinary southern hybridization washing step, i.e., a hybridization at a salt concentration corresponding to 60° C., 1×SSC, 0.1% SDS, preferably 60° C., 0.1×SSC, 0.1% SDS. The term "D-carbamylase activity" means any activity capable of producing D-amino acid by hydrolyzing an N-carbamyl-D-amino acid.

A DNA for encoding a protein which is identical substantially to the D-carbamylase encoded by the DNA described above is also a DNA according to the invention. Thus, the following (a) or (b) are in the scope of the present invention, where:

(a) is a DNA for encoding the amino acid sequence represented by Seq. ID No. 4 in the Sequence Listing,
(b) is a DNA for encoding a protein having D-hydantoinase activity which has an amino acid sequence resulting from the substitution, deletion, insertion, addition or inversion of one or several amino acid residues in the amino acid sequence represented by Seq. ID No. 4 in the Sequence Listing.

For the purpose of deducing, on the basis of the amino acid sequences (a) and (b) described above, a DNA for encoding such a sequence, a DNA base sequence universal codon can be employed. The term "several" means a number which results in no substantial deterioration of the steric structure or enzymatic activity of the protein, and which is typically 2 to 50, preferably 2 to 30, more preferably 2 to 10. The term "D-carbamylase activity" means any activity capable of producing D-amino acid by hydrolyzing an N-carbamyl-D-amino acid. Nevertheless, in the case of a protein involving such a substitution, deletion, insertion, addition or inversion in the amino acid sequence represented by Seq. ID No. 4 in the Sequence Listing, it is preferred that an enzymatic activity which is at least a half of that of the protein having the amino acid sequence represented by Seq. ID No. 4 in the Sequence Listing is possessed.

[III] Method for Producing D-hydantoinase and D-carbamylase:

A method for producing D-hydantoinase and D-carbamylase by a recombinant DNA technology is discussed below. A large number of the methods for producing useful proteins such as enzymes or physiologically active substances utilizing recombinant DNA technologies are known, and a use of the recombinant DNA technology allows a useful protein, which occurs naturally only in a trace amount, to be produced on a large scale.

Figure 2:
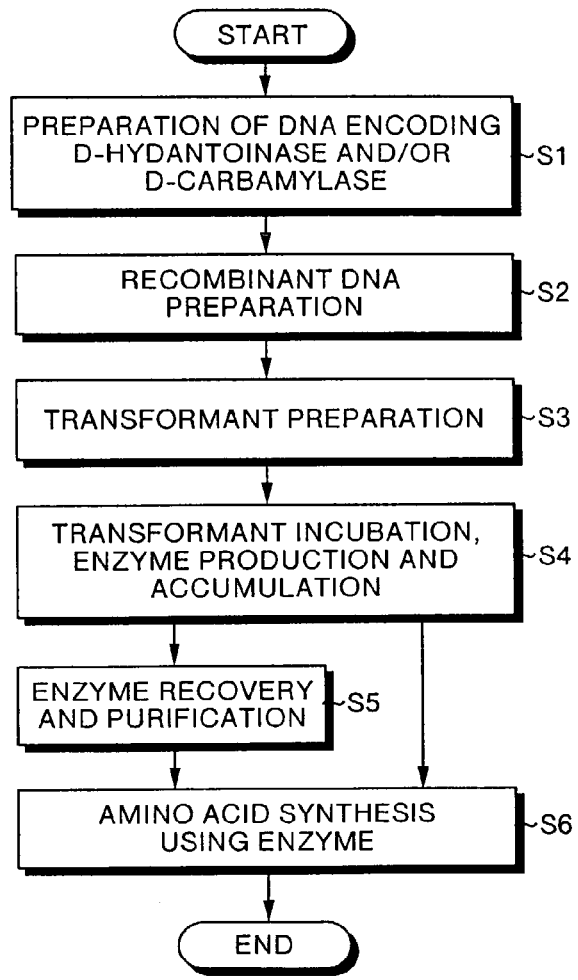
FIG. 2 is a flow chart of a process for producing D-hydantoinase and D-carbamylase according to the invention.

FIG. 2 shows a flow chart of a process for producing D-hydantoinase and D-carbamylase according to the invention.

First, D-hydantoinase DNA of the present invention and/or D-carbamylase DNA are prepared (Step S1).

Then, the prepared NDA is attached to a vector DNA to prepare a recombinant DNA (Step S2), and then a cell is transformed with the recombinant DNA to give a transformant (Step S3). Subsequently, the transformant is incubated in a culture medium to allow the D-hydantoinase and/or D-carbamylase to be produced and accumulated in the culture medium (Step S4).

In the following Step S5, the enzyme is recovered and purified, whereby accomplishing a large scale production of the D-hydantoinase and/or D-carbamylase.

An amino acid synthesis using the enzyme produced in Step S5 and the culture medium of Step S4 in which the enzyme in accumulated enables a large scale production of an intended amino acid (Step S6).

A DNA to be attached to a vector DNA may be any one allowing a D-hydantoinase of the present invention and/or D-carbamylase to be expressed.

A D-hydantoinase gene employed here to be attached to a vector DNA may for example be those already described above, that is:

(a) is the DNA having the base sequence represented by Seq. ID No. 1 in the Sequence Listing,
(b) is the DNA having a base sequence hybridizing with a complementary base sequence of the base sequence represented by Seq. ID No. 1 in the Sequence Listing under a stringent condition,
(c) is the DNA for encoding the amino acid sequence represented by Seq. ID No. 2 in the Sequence Listing, and
(d) is the DNA for encoding an amino acid sequence resulting from the substitution, deletion, insertion, addition or inversion of one or several amino acid residues in the amino acid sequence represented by Seq. ID No. 2 in the Sequence Listing.

A D-carbamylase gene employed here to be attached to a vector DNA may for example be those already described above, that is:

(a) is the DNA having the base sequence represented by Seq. ID No. 3 in the Sequence Listing,
(b) is the DNA having a base sequence hybridizing with a complementary base sequence of the base sequence represented by Seq. ID No. 3 in the Sequence Listing under a stringent condition,
(c) is the DNA for encoding the amino acid sequence represented by Seq. ID No. 4 in the Sequence Listing, and
(d) is the DNA for encoding an amino acid sequence resulting from the substitution, deletion, insertion, addition or inversion of one or several amino acid residues in the amino acid sequence represented by Seq. ID No. 4 in the Sequence Listing.

In addition to the DNAs listed above, a DNA in which a D-hydantoinase gene is ligated to a D-carbamylase may also be employed. In such a case, D-hydantoinase of the present invention and the D-carbamylase of the present invention are expressed simultaneously.

When a recombinant DNA technology is employed to produce a protein on a large scale, a host cell to be transformed may for example be a bacterial cell, actinomyces cell, yeast cell, fungal cell, plant cell, animal cell and the like. Since technologies for producing proteins on large scales using coliform microorganisms have extensively been reported, such a coliform microorganism, especially *Escherichia coli*, is employed generally. A method for producing D-hydantoinase and/or D-carbamylase using a transformed coliform microorganism is discussed below.

A promoter for expressing a DNA for encoding a D-hydantoinase and/or D-carbamylase may be a promoter employed usually for producing a protein in a coliform microorganism, which may for example be a potent promoter such as a T7 promoter, trp promoter, lac promoter, tac promoter, PL promoter and the like.

Also for the purpose of increasing the production, it is preferable to ligate a terminator which is a transcription termination sequence to the downstream of the protein gene. Such a terminator may for example be a T7 terminator, fd phage terminator, T4 terminator, tetracyclin resistant gene terminator, coliform trpA gene terminator and the like.

A vector for transducing a gene encoding a hydantoinase and/or D-carbamylase into a host cell is preferably be one of a multicopy type, such as a plasmid having a replication initiating point derived from Col E1, for example, a pUC plasmid or pBR322 plasmid or a derivative thereof. The term "derivative" employed here is a plasmid which has been subjected to an alteration by the substitution, deletion, insertion, addition or inversion of bases. The alteration referred here means to include an alteration by a mutating treatment using a mutating agent or UV irradiation as well as a spontaneous mutation.

For the purpose of screening for a transformant, the vector having a marker such as an ampicillin resistant gene is employed preferably, such as a plasmid available as an expression vector having a potent promoter, for example, a pUC (Takara Shuzo Co., Ltd.), pPROK (Clonetech), pKK233-2 (Clonetech) and the like.

A DNA fragment in which a promoter, a gene encoding a hydantoinase and/or D-carbamylase and a terminator are ligated in this order is then ligated to a vector DNA to obtain a recombinant DNA.

The recombinant DNA is employed to transform a host cell, and then the cell is incubated, resulting in the expression and production of the hydantoinase and/or D-carbamylase. As a method for effecting a transformation and a method for screening for a transformant, those described in Molecular Cloning, 2nd edition, Cold Spring Harbor press (1989) are applicable.

As a production medium, a culture medium employed ordinarily for incubating a coliform microorganism such as a M9-casamino acid medium and LB medium may be employed. The incubation condition and the production inducing condition are selected appropriately depending on the types of the marker of the vector, promoter and host cell employed. In order to increase the production of the enzyme, it is also preferred to add isopropyl 1-thio-β-D-galactopyranoside (IPTG) to the culture medium or to conduct an enzyme inducing treatment such as warming.

After recovering a cultured cell for example by a centrifugation, the cell is crushed or subjected to lysis to recover the hydantoinase and/or D-carbamylase, which can be used as a crude enzyme solution. The cell can be crushed by an ultrasonication, French press crushing, glass bead crushing, and the like, or may be subjected to lysis using an albumen lysozyme, peptidase treatment, or a combination thereof. If necessary, the enzyme may be purified by an ordinary procedure such as a precipitation, filtration and column chromatography. In such a case, a purification utilizing an antibody against the enzyme itself can also be utilized.

A D-hydantoinase according to the invention obtained by a recombinant described above is a protein having D-hydantoinase activity which has an amino acid sequence represented by (a) or (b), where:
(a) is the amino acid sequence represented by Seq. ID No. 2 in the Sequence Listing,
(b) is the amino acid sequence resulting from the substitution, deletion, insertion, addition or inversion of one or several amino acid residues in the amino acid sequence represented by Seq. ID No. 2 in the Sequence Listing.

A D-carbamylase according to the invention obtained by a recombinant described above is a protein having D-carbamylase activity which has an amino acid sequence represented by (c) or (d), where:
(c) is the amino acid sequence represented by Seq. ID No. 4 in the Sequence Listing,
(d) is the amino acid sequence resulting from the substitution, deletion, insertion, addition or inversion of one or several amino acid residues in the amino acid sequence represented by Seq. ID No. 4 in the Sequence Listing.

The definitions of the terms "several", "D-hydantoinase activity" and "D-carbamylase activity" employed here are synonymous with those described in [I] DNA for encoding D-hydantoinase and D-carbamylase.

[III] Method for Producing D-amino Acid

A method for producing D-amino acid employing a hydantoinase and/or D-carbamylase according to the invention is discussed below.

A method for producing D-amino acid according to the invention employs the enzymes of the present invention as at least one of hydantoinase and carbamylase, the combination of which may be one of the three shown below. That is,
(i) D-hydantoinase of the present invention+carbamylase,
(ii) Hydantoinase +carbamylase of the present invention, and
(iii) D-hydantoinase of the present invention+carbamylase of the present invention.

In the case of combination (i), a D-hydantoinase may for example be a protein having D-hydantoinase activity which has an amino acid sequence represented by (a) or (b), where:
(a) is the amino acid sequence represented by Seq. ID No. 2 in the Sequence Listing,
(b) is the amino acid sequence resulting from the substitution, deletion, insertion, addition or inversion of one or several amino acid residues in the amino acid sequence represented by Seq. ID No. 2 in the Sequence Listing.

It is also possible that a DNA for encoding such a D-hydantoinase is attached to a vector to form a recombinant DNA by which a cell is then transformed and the cell is incubated to yield a D-hydantoinase for use. When a transformed cell is used to produce a D-hydantoinase, a substrate may be added directly to the culture medium during the incubation, or the cell or washed cell recovered from the culture medium may be employed. A cell treatment product obtained by crushing or being subjected to lysis may be employed as it is, or a D-hydantoinase may be recovered from the cell treatment product and used as a crude enzyme solution or maybe purified before use. Thus, any fraction containing D-hydantoinase activity can be employed.

A substrate for a D-hydantoinase according to the invention may be any 5-substituted hydantoin compound capable of being hydrolyzed at the substrate specificity of this enzyme. Those which may be exemplified are a 5-substituted hydantoin compound corresponding to a natural amino acid such as hydantoin, 5-methylhydantoin, 5-benzylhydantoin, 5-(4-hydroxybenzyl)hydantoin, 5-indolylmethylhydantoin, 5-(3,4-dihydroxybenzyl)hydantoin, 5-methylthioethylhydantoin, 5-isopropylhydantoin, 5-isobutylhydantoin, 5-sec-butylhydantoin, 5-(4-aminobutyl)hydantoin, 5-hydroxymethylhydantoin and the like, as well as a 5-substituted hydantoin compound corresponding to a non-natural amino acid or a derivative thereof, such as 5-phenylhydantoin, 5-(4-hydroxyphenyl)hydantoin, 5-methoxymethylhydantoin, 5-benzyloxymethylhydantoin, 5-(3,4-methylenedioxybenzyl) hydantoin, dihydrouracil and the like.

A carbamylase to be combined with a D-hydantoinase of the present invention may be any known enzyme capable of catalyzing a reaction which effects hydrolitycally on an N-carbamyl-D-amino acid to yield a D-amino acid or a material containing such an enzyme. Thus, it may be a carbamylase acting specifically on an N-carbamyl-D-amino acid (D-carbamylase) or a non-optically selective carbamylase. The term "material containing an enzyme" employed here means a material containing the enzyme, such as those containing a culture medium, cultured cell, cell treatment product obtained by crushing the cell or subjecting the cell to a lysis, crude enzyme solution or purified enzyme.

A D-carbamylase is known to be present for example in *Pseudomonas* or *Agrobacterium* microorganisms (Japanese Patent 2902112).

Combination (ii) is discussed below. AD-carbamylase of the present invention may for example be a protein having D-carbamylase activity which has an amino acid sequence represented by (a) or (b), where:
(a) is the amino acid sequence represented by Seq. ID No. 4 in the Sequence Listing,
(b) is the amino acid sequence resulting from the substitution, deletion, insertion, addition or inversion of one or several amino acid residues in the amino acid sequence represented by Seq. ID No. 4 in the Sequence Listing.

It is also possible that a DNA for encoding such a D-carbamylase is attached to a vector to form a recombinant DNA by which a cell is then transformed and the cell is incubated to yield a D-carbamylase for use. When a transformed cell is used to produce a D-carbamylase, a substrate may be added directly to the culture medium during the incubation, or the cell or washed cell recovered from the culture medium may be employed. A cell treatment product obtained by crushing or being subjected to lysis may be employed as it is, or a D-carbamylase may be recovered from the cell treatment product and used as a crude enzyme solution or may be purified before use. Thus, any fraction containing D-carbamylase activity can be employed.

A substrate for a D-carbamylase according to the invention may be any N-carbamyl-D-amino acid capable of being hydrolyzed at the substrate specificity of this enzyme. Thus, an N-carbamyl-D-amino acid other than the N-carbamyl-D-amino acids obtained from the 5-substituted hydantoin compounds listed above can also be employed as a substrate.

A hydantoinase to be combined with a D-carbamylase of the present invention may be any known enzyme capable of catalyzing a reaction which effects hydrolitycally on a 5-substituted hydantoin compound to yield an N-carbamylamino acid or a material containing such an enzyme. The term "material containing an enzyme" employed here means a material containing the enzyme, such as those containing a culture medium, cultured cell, cell treatment product obtained by crushing the cell or subjecting the cell to a lysis, crude enzyme solution or purified enzyme. Nevertheless, since a D-carbamylase of the present invention is D-form-specific, a non-optically specific hydantoinase or a D-hydantoinase acting specifically on a D form should be employed. A non-optically specific hydantoinase known to be present for example in *Microbacterium liquefaciens* strain AJ3912 (Japanese Patent Application No. 2001-298619) A D-hydantoinase which acts specifically on a hydantoin in the D form is known to be present for example in *Agrobacterium* sp. Strain AJ11220 (Japanese Patent Application Publication No. 56-003034). *Microbacterium liquefaciens* strain AJ3912 was a microorganism which was deposited on Jun. 27, 1975 in National Institute of Bioscience and Human-Technology, Ministry of Economy, Trade and Industry, METI, and received the acceptation number FERM-P3133. Later, on Jun. 27, 2001, the same strain has been deposited as FERM BP-7643 based on Budapest convention. *Agrobacterium* sp. Strain AJ11220 (FERM-P4347) was a microorganism which had initially been deposited under the name of *Pseudomonas* sp. on Dec. 20, 1977 in National Institute of Bioscience and Human-Technology, Ministry of Economy, Trade and Industry, METI, but was subsequently re-identified to be classified in *Agrobacterium* sp. Currently, it is deposited in the International Patent Organism Depositary of National Institute of Advanced Industrial Science and Technology as *Agrobacterium* sp. Strain AJ11220 (National deposit No. FERM-P4347, International deposit No. FERM BP-7645).

In Combination (iii), a D-hydantoinase of the present invention described in the section of Combination (i) and a D-carbamylase of the present invention described in the section of Combination (ii) are combined. Among Combination (I) to (iii), the most preferred combination is Combination (iii).

In the reaction process employed here, a mixture of a D-hydantoinase and D-carbamylase may act on a 5-substituted hydantoin compound, or a D-hydantoinase may first act on a 5-substituted hydantoin compound which is then subjected to the action of a D-carbamylase. The former process is preferred for the purpose of the simplification of the reaction process.

When producing D-amino acid by a method employing any of Combination (i) to (iii) described above, it is possible to produce an N-carbamylamino acid or amino acid in the L form. For example, a D-hydantoinase of the present invention is employed to produce an N-carbamyl-D-amino acid from a DL-5-substituted hydantoin, and then the remaining L-5-substituted hydantoin is separated from the N-carbamyl-D-amino acid to recover the L-5-substituted hydantoin, which is then hydrolyzed to yield an N-carbamyl-L-amino acid, which is further hydrolyzed to yield an L-amino acid. Although such a hydrolyzing reaction may employ a hydrolyzing enzyme acting on an L form, a chemical hydrolyzing treatment for example with nitrous acid also enables the production of an L-amino acid at a high yield with preserving the optical activity.

When converting a DL-5-substituted hydantoin compound into a D-amino acid, the D-amino acid can be produced at a molar yield of 50% or higher from the DL-5-substituted hydantoin compound by means of a combination of the spontaneous racemization or chemical racemization of a 5-substituted hydantoin compound, or the racemization employing a hydantoin racemase.

In other words, it is preferred to use a hydantoin racemase in addition to a D-hydantoinase and D-carbamylase. Such a hydantoin racemase is preferably the hydantoin racemase derived from *Microbacterium liquefaciens* strain AJ3912 (FERM-P3133) described in Japanese Patent Application 2001-278739. In such a case, a D-amino acid can be produced theoretically at 100% molar yield from a DL-5-substituted hydantoin compound since a hydantoin racemase contained in a protein mixture catalyzes the racemization of the 5-substituted hydantoin compound as shown in the following scheme.

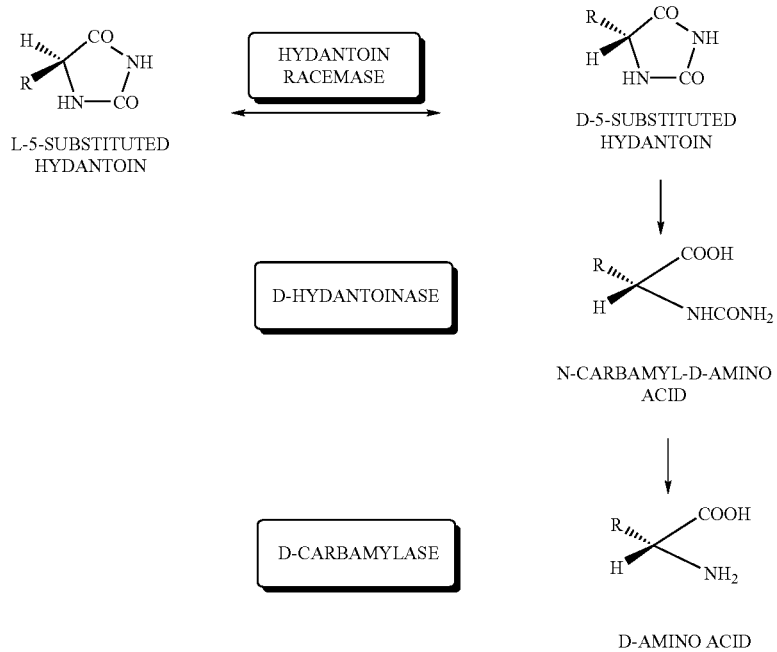

It is also possible to produce an N-carbamylamino acid using the protein mixture described above. For example, the N-carbamylamino acid can be produced by interrupting the hydrolysis reaction at the stage of the N-carbamylamino acid by adding, for example, a D-carbamylase inhibitor to the protein mixture described above.

When an amino acid producing reaction is allowed to proceed using a culture medium of a cell transformed by a recombinant DNA obtained by ligating a DNA for encoding a D-hydantoinase of the present invention and/or D-carbamylase with a vector, isolated cell, washed cell, cell treatment product, crude enzyme solution or purified enzyme solution obtained from the cell treatment product, then a reaction mixture containing the 5-substituted hydantoin compound and the culture medium, isolated cell, washed cell, cell treatment product, crude enzyme solution or purified enzyme solution is kept at an appropriated temperature of 25 to 60° C. at pH 5 to 9 while allowing to stand or stir for 8 hours to 5 days.

When an amino acid producing reaction is allowed to proceed while incubating a cell transformed by a recombinant DNA obtained by ligating a DNA for encoding a D-hydantoinase of the present invention and/or D-carbamylase with a vector in an aqueous medium, an aqueous medium containing a 5-substituted hydantoin compound together with nutrient components essential for the growth of the transformed cell such as carbon sources, nitrogen sources, inorganic ions and the like is employed. The addition of organic trace nutrient components such as vitamins and amino acids may frequently lead to a satisfactory result. It is also possible to add the 5-substituted hydantoin compound in portions. It is preferred to conduct the incubation in an aerobic condition at pH 5 to 9 at an appropriated temperature of 25 to 40° C. for 8 hours to 5 days.

The D-amino acid in a culture medium a reaction mixture can rapidly be quantified by a known method. Thus, for convenience, a thin layer chromatography using for example a HPTLC CHIR manufactured by Merck can be utilized, and, for obtaining a further higher analytical accuracy, a high pressure liquid chromatography (HPLC) employing an optical resolution column such as a CHIRALPAK WH manufactured by DAICEL CHEMICAL INDUSTRIES, LTD. can be employed.

A D-amino acid accumulated in a culture medium or reaction mixture can be collected from the culture medium or reaction mixture by a standard method. For example, procedures such as filtration, centrifugation, concentration under vacuum, ion exchange or adsorption chromatography, crystallization and the like, may be employed if necessary in combination with each other. Especially after converting from a 5-substituted hydantoin compound at a high concentration, the D-amino acid can readily be isolated as a crystal by cooling the culture medium or reaction mixture and adjusting the pH.

The present invention is further described in the following examples, which are not intended to restrict the invention. The quantification and the optical purity assay of a 5-substituted hydantoin compound, N-carbamylamino acid and amino acid in an example are conducted using HPLC employing an optical resolution column, CHIRALPAK WH, manufactured by DAICEL CHEMICAL INDUSTRIES, LTD. The analytical condition is described below.

Column, CHIRALPAK WH 0.46 cm φ×25 cm (DAICEL CHEMICAL INDUSTRIES, LTD.)

Mobile phase: 5% (v/v) Methanol, 1 mM $CuSO_4$
Column temperature: 50° C.
Flow rate: 1.5 ml/min
Detection: $UV_{210}$

EXAMPLE 1

Isolation of D-hydantoinase Gene and D-carbamylase Gene from AJ11221 Microorganism 1. Cell Preparation

*Pasteurella pneumotropica* strain AJ11221 was incubated in a CM2G agar medium (glucose 0.5%, yeast extract 1.0%, peptone 1.0%, NaCl 0.5%, Agar 2%, pH 7.0) at 30° C. for 24 hours, whereby being refreshed. One "spatulaful" of the culture medium was inoculated to a 500 mL Sakaguchi flask containing 50 ml of a CM2G liquid medium, which was then incubated aerobically with shaking at 30° C. for 16 hours.

2. Collection of Chromosomal DNA from Cell 50 ml of the culture medium was centrifuged (12,000×G, 4° C., 15 minutes) and the cell was collected. The cell was then washed by suspending in 10 ml of 50:20 TE (50 mM Tris-HCl, (pH 8.0), 20 mM EDTA) and recovered by centrifugation, and then re-suspended in 10 ml of 50:20 TE. To this suspension, 0.5 ml of a 20 mg/ml lysozyme solution and 1 ml of a 10% SDS solution were added, and the mixture was incubated at 55° C. for 20 minutes. After the incubation, one volume of 10:1 TE-saturated phenol was added to remove proteins. To the separated water layer, one volume of 2-propanol was added to precipitate a DNA for recovery. The precipitated DNA was dissolved in 0.1 ml of 50:20 TE, to which 5 µl of 10 mg/ml RNase and 5 µl of 10 mg/ml Proteinase K were added, and the mixture was reacted at 55° C. for 20 minutes. After the reaction, proteins were removed using one volume of 10:1 TE-saturated phenol. To the separated water layer, one volume of 24:1 chloroform/isoamyl alcohol was added, and the mixture was stirred and then the water layer was recovered. This procedure was repeated twice and then the resultant water layer was supplemented with a 3M sodium acetate solution (pH 5.2) at the final concentration of 0.4 M, and two volumes of ethanol was then added. The precipitated DNA was recovered, washed with 70% ethanol, dried, and then dissolved in 1 ml of 10:1 TE.

3. Isolation of D-carbamylase from Gene Library

200 µg of the chromosomal DNA of *Pasteurella pneumotropica* strain AJ11221 was supplemented with 1U of a restriction enzyme Sau3AI, and the mixture was reacted at 37° C. for 15 minutes to effect a partial digestion. Then, from this DNA 3 to 8 kbp fragments were recovered by an agarose electrophoresis. The fragments were ligated with BamHI digestion products of a plasmid pUC18, whereby transforming an *Esherichia coil* strain JM109 to prepare a gene library. The library was plated onto an ampicillin-supplemented LB medium (tryptone 1%, yeast extract 0.5%, sodium chloride 1%, ampicillin 0.01%, agar 2%, pH 7.0), and then a colony was inoculated in a liquid medium containing as the only nitrogen source N-carbamyl-D-phenylalanine (glucose 0.2%, N-carbamyl-D-phenylalanine 0.2%, $Na_2HPO_4$ 0.6%, $KH_2PO_4$ 0.3%, NaCl 0.05%, $MgSO_4$ 0.012%, $CaCl_2$ 0.1 mM, ampicillin 0.01%, thiamine 0.0001%, pH 7.0) to effect an enrichment culture and then a strain capable of growing with N-carbamyl-D-phenylalanine as the only nitrogen source was selected. A transformant thus obtained was isolated and subjected to an incubation on an LB medium containing ampicillin and isopropyl-1-thio-β-D-galactopyranoside (IPTG), followed by centrifugation and cell collection, and then the cell was added at 1% to a 0.1 M phosphate buffer solution containing 0.5% N-carbamyl-D-phenylalanine and allowed to react at 37° C. for 5 hours. The reaction mixture was analyzed and D-phenylalanine was revealed to be produced, whereby assuring that this transformant contained the plasmid containing the intended gene. From this transformant, a plasmid DNA was prepared and designated as pUC413-1.

4. Base Sequence of Inserted Fragment

The base sequence of an inserted fragment of the plasmid pUC413-1 was determined by a dideoxy method, and is shown as Sequence ID No. 5 in the Sequence Listing. As a result, the length of the inserted fragment was 2.8 kbp and the open reading frame of about 0.9 kb (ORF1; Base No. 1141 to 2064) was proven to be contained (FIG. 1).

5. Homology Between ORF1 and Known Sequence

ORF1 was characterized for the homology to known sequences, and proven to exhibit the homology of 78% (81% in amino acid sequence) to a known *Agrobacterium* microorganism-derived D-carbamylase gene and the homology of 67% (59% in amino acid sequence) to *Pseudomonas* microorganism-derived D-carbamylase gene. As a result, ORF1 was assumed to contain a D-carbamylase gene. However, any sequence exhibiting a homology to a D-hydantoinase was not found. The base sequence of the entire length of the D-carbamylase is shown as Sequence ID No. 3 in the Sequence Listing, and the corresponding amino acid sequence is shown as Sequence ID No. 4 in the Sequence Listing.

6. Isolation of D-hydantoinase Gene From Gene Library

Accordingly, a D-hydantoinase gene was isolated using a gene library of *Pasteurella pneumotropica* strain AJ11221 prepared in Section 3 described above. For a screening, a transformant was cultured on an LB plate containing ampicillin, transferred to a pH indicator-supplemented screening plate (D-5-benzylhydantoin 0.5%, cresol red 0.005%, MnCl$_2$ 1 mM, agar 2%, pH 8.5), and screened for a strain exhibiting the change in the color of the pH indicator in response to the production of N-carbamyl-D-phenylalanine. This transformant was used to prepare a plasmid containing a D-hydantoinase gene, which was then designated as pUC413-2.

7. Base sequence of Inserted Fragment

The base sequence of an inserted fragment of the plasmid pUC413-2 was determined by a dideoxy method, and is shown as Sequence ID No. 6 in the Sequence Listing. As a result, the length of the inserted fragment was 2.3 kbp and the open reading frame of about 1.4 kb (ORF2; Base No. 184 to 1572) was proven to be contained (FIG. 1).

8. Homology Between ORF2 and Known Sequence

ORF2 was characterized for the homology to known sequences, and proven to exhibit the homology of 77% (76% in amino acid sequence) to a *Agrobacterium* microorganism-derived D-hydantoinase gene. As a result, ORF2 was assumed to contain a D-hydantoinase gene. The base sequence of the entire length of the D-hydantoinase is shown as Sequence ID No. 1 in the Sequence Listing, and the corresponding amino acid sequence is shown as Sequence ID No. 2 in the Sequence Listing.

EXAMPLE 2

Expression of Strain AJ11221-Derived D-hydantoinase Gene and D-carbamylase Gene in *E.coli*

1. Construction of Expression Plasmid

In order to express the both genes in *E.coli*, plasmids pUC413H and pUC413C in which the both genes were ligated to the downstream of the lac promoter of pUC18 were constructed as follows. First, a chromosomal DNA of *Pasteurella pneumotropica* strain AJ11221 was employed as a template to amplify each gene by a PCR using the oligonucleotides shown in Table 1 as primers. Each of these fragments was digested with XbaI/HindIII and EcoRI/XbaI and ligated to the XbaI/HindIII and EcoRI/XbaI digestion product of pUC18, and then transduced into *E.coli* JM109. The ampicillin resistant strains were screened for strains having intended plasmids, which were designated as expression plasmids pUC413H and pUC413C.

TABLE 1

Primers employed for amplifying D-hydantoinase gene and D-carbamylase gene derived from strain AJ11221

| | | |
|---|---|---|
| Hydantoinase | 5'-end CGC<u>TCTAGA</u>GGGAGACTGACG<u>ATG</u>GATCTCATCGT<br>XbaI Initiation codon | Sequence ID No. 7 |
| | 3'-end CGC<u>AAGCTT</u>CCTCTGACGCGGCGAATG<br>HindIII | Sequence ID No. 8 |
| Carbamylase | 5'-end CGCG<u>AATTC</u>CATCGAACCAGGGAGGATTTTGGA<br>EcoRI | Sequence ID No. 9 |
| | 3'-end CGC<u>TCTAGA</u>CGCCCG<u>CTA</u>GCGGACCTGTT<br>XbaI Termination codon | Sequence ID No. 10 |

2. Preparation of Cell-Free Extract

Each of an *E.coli* transformant having pUC632H and an *E.coli* transformant having pUC632C was seed-cultured for 16 hours at 37° C. in an LB medium containing 0.1 mg/ml ampicillin. 1 ml of this seed culture was added to a 500 ml Sakaguchi flask containing 50 m of an LB medium, to which 1 ml of the seed culture was added, and the mixture was major-cultured at 37° C. 2.5 hours after initiating the incubation, IPTG was added at the final concentration of 1 mM, and the incubation was continued further for 4 hours.

After completing the incubation, the cells were collected, washed, and suspended in 5 ml of 50 mM KBP (pH 8,0) and crushed using bead heater for 3 minutes (30 seconds×6 cycle, at 90 seconds interval) together with 0.1 mm φ glass beads. The solution was recovered, centrifuged at 20,000 G for 10 minutes, and the supernatant was obtained as a cell-free extract.

3. D-hydantoinase and D-carbamylase Activity Assay

The assay of the D-hydantoinase activity was conducted by incubating a reaction mixture containing 120 mg/dl D-5-benzylhydantoin (BH), 50 mM KPB (pH 8.0) and an enzyme solution at 37° C. for 30 minutes, adding 9 volumes of 1.1 mMCuSO$_4$, 11.1 mM H$_3$PO$_4$, centrifuging at 20,000G for 10 minutes to remove the pellet, and then quantifying the resultant N-carbamylphenylalanine (N—Car—Phe) by HPLC. One unit of the enzyme activity was defined as an enzymatic activity capable of producing 1 μmol of N-carbamylphenylalanine per 1 minute under the condition described above.

The assay of the D-carbamylase activity was conducted by incubating a reaction mixture containing 80 mg/dl N-carbamyl-D-phenylalanine, 50 mM KPB (pH 7.5) and an enzyme solution at 37° C. for 30 minutes, adding 9 volumes of 1.1 mMCuSO$_4$, 11.1 mM H$_3$PO$_4$, centrifuging at 20,000G for 10 minutes to remove the pellet, and then quantifying the resultant N-phenylalanine (D—Phe) by HPLC. One unit of the enzyme activity was defined as an enzymatic activity capable of producing 1 μmol of N-phenylalanine per 1 minute under the condition described above.

The results are shown in Table 2. Since the strain transformed by pUC413H exhibited D-hydantoinase activity and the strain transformed by pUC413C exhibited D-carbamylase activity, it was proven that the both genes were a D-hydantoinase gene and D-carbamylase gene derived from *Pasteurella pneumotropica* strain AJ11221 and were expressed in the cell of *E.coli*.

TABLE 2

Enzymatic activity of cell-free extract of *E. coli* having pUC413H and pUC413C

| Plasmid | IPTG supplement | D-Hydantoinase activity (U/mg) | D-Carbamylase activity (U/mg) |
|---|---|---|---|
| pUC413H | + | 0.11 | Not detected |
|  | − | 0.01 | Not detected |
| pUC413C | + | Not detected | 0.15 |
|  | − | Not detected | 0.02 |
| pUC18 | + | Not detected | Not detected |
|  | − | Not detected | Not detected |

EXAMPLE 3

Production of D-phenylalanine Using Washed *E.coli* Cell

Washed cells of JM109/pUC413H and JM109/pUC413C incubated similarly to Example 2 were prepared, added each at 1 g/dl to 0.1 mM KPB (pH 7.5) containing 1 g/dl of D-5-benzylhydantoin and reacted at 30° C. By sampling at 24 hours after the reaction followed by centrifugation followed by analysis of the supernatant by HPLC, D-phenylalanine produced was quantified.

The results are shown in Table 3. As evident from this table, by using the washed *E.coli* cells in which the D-hydantoinase gene and D-carbamylase gene were expressed, D-phenylalanine was produced efficiently from benzylhydantoine.

TABLE 3

D-Phenylalanine production using washed *E. coli* cells

| D-Hydantoinase gene-expressing strain | D-Carbamylase gene-expressing strain | Phenylalanine production level (g/dl) |
|---|---|---|
| JM109/pUC413H | JM109/pUC413C | 0.31 |
| JM109/pUC18 | JM109/pUC18 | 0.00 |

EXAMPLE 4

Production of D-amino Acid Using Washed *E.coli* Cell

Washed cells of JM109/pUC413H and JM109/pUC413C prepared similarly to Example 3 were added each at 1 g/dl to 0.1 mM KPB (pH 7.5) containing 1 g/dl of each of 5-substituted hydantoin compounds, and reacted at 30° C. By sampling 24 hours after the reaction followed by centrifugation followed by analysis of the supernatant by HPLC, the resultant each amino acid was quantified.

The results are shown in Table 4. As evident from this table, by using the washed *E.coli* cells in which the D-hydantoinase gene and D-carbamylase gene were expressed, each D-amino acid was produced efficiently from each 5-substituted hydantoin compound.

TABLE 4

D-Amino acid production using washed *E. coli* cells

| 5-Substituted hydantoin compound | Produced amino acid | Production level (g/dl) |
|---|---|---|
| D-5-(4-Hydroxybenzyl)hydantoin | D-Tyrosine | 0.12 |
| D-5-Indolylmethylhydantoin | D-Tryptophan | 0.10 |
| D-5-Methylthioethylhydantoin | D-Methionine | 0.28 |
| Hydantoin | D-Glycine | 0.08 |
| D-5-Methylhydantoin | D-Alanine | 0.03 |
| D-5-Isopropylhydantoin | D-Valine | 0.06 |
| D-5-Isobutylhydantoin | D-Leucine | 0.01 |
| D-5-sec-Butylhydantoin | D-Isoleucine | 0.01 |
| D-5-(4-Aminobutyl) hydantoin | D-Lysine | 0.05 |
| D-5-Carboxyethylhydantoin | D-Glutamic acid | 0.04 |
| D-5-Phenylhydantoin | D-Phenylglycine | 0.30 |
| D-5-(4-Hydroxyphenyl)hydantoin | D-4-Hydroxyphenyl glycine | 0.23 |

EXAMPLE 5

D-phenylalanine Production when Combined with Racemization with Hydantoin Racemase An *E.coli* transformant having a plasmid pUCFHR containing a hydantoin racemase gene derived from *Microbacterium liquefaciens* strain AJ3912 (FERM-P3133) described in Japanese Patent Application No. 2001-278739 was seed-cultured for 16 hours at 37° C. in an LB medium containing 0.1 mg/ml of ampicillin. 1 ml of this seed culture was added to a 500 ml Sakaguchi flask containing 50 ml of an LB medium, to which 1 ml of the seed culture was added, and the mixture was major-cultured at 37° C. 2.5 hours after initiating the incubation, IPTG was added at the final concentration of 1 mM, and the incubation was continued further for 4 hours. After completing the incubation, the cell was collected, washed, whereby preparing a washed cell.

On the other hand, washed cells of JM109/pUC413H and JM109/pUC413C were prepared similarly to Example 3, added each at 1 g/dl, together with the washed cell of the hydantoin racemase-expressing strain described above, to 0.1 mM KPB (pH 7.5) containing 1 g/dl of DL-5-benzyl-hydantoin and reacted at 30° C. By sampling at 24, 48 and 72 hours after the reaction followed by centrifugation followed by analysis of the supernatant by HPLC, D-phenylalanine produced was quantified.

The results are shown in Table 5. As evident from this table, by using the washed E.coli cells in which the hydantoin racemase gene, D-hydantoinase gene and D-carbamylase gene were expressed, D-phenylalanine was produced efficiently from benzylhydantoine in the DL form.

TABLE 5

D-Phenylalanine production when combined with racemization by hydantoin racemase

| Hydantoin racemase gene-expressing strain | D-Hydantoinase gene-expressing strain | D-Carbamylase gene-expressing strain | Phenylalanine production level (g/dl) |
|---|---|---|---|
| JM109/pUCFHR | JM109/pUC413H | JM109/pUC413C | 0.83 |
| JM109/pUC18 | JM109/pUC18 | JM109/pUC18 | 0.00 |

EXAMPLE 6

A reaction was performed similarly to Example 5 to obtain 500 ml of the reaction solution containing D-phenylalanine. This reaction solution was centrifuged (10,000G× 10 minutes) to separate the cells, and the supernatant was concentrated under reduced pressure to 20 ml, whereby precipitating a crystal of D-phenylalanine. The precipitated crystal was recovered by filtration through a paper filter to obtain a crude crystal. The crude crystal (2.4 g) was dissolved by combining with 10 ml of water and 1 ml of concentrated sulfuric acid, to which 100 mg of activated carbon was added to decolorize the solution. Then, the activated carbon was filtered off, and the filtrate was combined with 5 ml of a 28% aqueous ammonia to adjust at pH 3.5, whereby precipitating D-phenylalanine. Subsequently, the precipitated crystal was recovered by filtration through a filter paper and dried to yield 1.8 g of D-phenylalanine. An HPLC analysis revealed that the material purity was 99% and the optical purity was 99% e.e. or higher.

According to the present invention, a D-hydantoinase gene and D-carbamylase gene can be expressed stably in a large amount in a host cell such as a coliform microorganism. As a result, such an enzyme can readily be prepared using such a transformant, resulting in an ability of producing a D-amino acid useful in pharmaceuticals, chemical industrial products and food additives efficiently using such a transformant, extract therefrom as well as a purified enzyme and the like.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An isolated DNA having a base sequence represented by (a) or (b) and that encodes a protein having D-hydantoinase activity, wherein
   (a) is the base sequence represented by SEQ ID NO: 1 in the Sequence Listing; and
   (b) is a base sequence hybridizing with a complementary base sequence of the base sequence represented by SEQ ID NO: 1 in the Sequence Listing at a salt concentration corresponding to 0.1×SSC, 0.1% SDS at 60°C.

2. The DNA of claim 1, wherein the base sequence is represented by (a).

3. The DNA of claim 1, wherein the base sequence is represented by (b).

4. An isolated DNA encoding a protein having D-hydantoinase activity and having an amino acid sequence represented by (c) or (d), wherein
   (c) is the amino acid sequence represented by SEQ ID NO: 2 in the Sequence Listing;
   (d) is an amino acid sequence resulting from the substitution, deletion, insertion, addition or inversion of one to ten amino acid residues in the amino acid sequence represented by SEQ ID NO: 2 in the Sequence Listing.

5. The DNA of claim 4, wherein the amino acid sequence is represented by (c).

6. The DNA of claim 4, wherein the amino acid sequence is represented by (d).

7. A recombinant DNA resulting from a connection of a DNA with a vector DNA, wherein
   the DNA has a base sequence represented by (a) or (b) and encodes a protein having D-hydantoinase activity, wherein
   (a) is the base sequence represented by SEQ ID NO: 1 in the Sequence Listing; and
   (b) is a base sequence hybridizing with a complementary base sequence of the base sequence represented by SEQ ID NO: 1 in the Sequence Listing at a salt concentration corresponding to 0.1×SSC, 0.1% SDS at 60° C.

8. The recombinant DNA of claim 7, wherein the vector DNA is derived from a pUC plasmid, pBR322 plasmid or a derivative thereof.

9. The recombinant DNA of claim 7, wherein the base sequence is represented by (a).

10. The recombinant DNA of claim 7, wherein the base sequence is represented by (b).

11. A recombinant DNA resulting from a connection of a DNA with a vector DNA, wherein
    the DNA encodes a protein having D-hydantoinase activity and having an amino acid sequence represented by (c) or (d), wherein
    (c) is the amino acid sequence represented by SEQ ID NO: 2 in the Sequence Listing;
    (d) is an amino acid sequence resulting from the substitution, deletion, insertion, addition or inversion of one to ten amino acid residues in the amino acid sequence represented by SEQ ID NO: 2 in the Sequence Listing.

12. The recombinant DNA of claim 11, wherein the vector DNA is derived from a pUC plasmid, pBR322 plasmid or a derivative thereof.

13. The recombinant DNA of claim 11, wherein the amino acid sequence is represented by (c).

14. The recombinant DNA of claim 11, wherein the amino acid sequence is represented by (d).

15. A cell transformed with a recombinant DNA resulting from a connection of a DNA with a vector DNA, wherein
    the DNA has a base sequence represented by (a) or (b) and encodes a protein having D-hydantoinase activity, wherein
    (a) is the base sequence represented by SEQ ID NO: 1 in the Sequence Listing; and
    (b) is a base sequence hybridizing a complementary base sequence of with the base sequence represented by SEQ ID NO: 1 in the Sequence Listing at a salt concentration corresponding to 0.1×SSC, 0.1% SDS at 60° C.

16. The cell of claim 15, wherein the cell is derived from *Escherichia coli*.

17. The cell of claim 15, wherein the base sequence is represented by (a).

18. The cell of claim 15, wherein the base sequence is represented by (b).

19. A cell transformed with a recombinant DNA resulting from a connection of a DNA with a vector DNA, wherein
the DNA encodes a protein having D-hydantoinase activity and having an amino acid sequence represented by (c) or (d), wherein
(c) is the amino acid sequence represented by SEQ ID NO: 2 in the Sequence Listing;
(d) is an amino acid sequence resulting from the substitution, deletion, insertion, addition or inversion of one to ten amino acid residues in the amino acid sequence represented by SEQ ID NO: 2 in the Sequence Listing.

20. The cell of claim 19 wherein the cell is derived from *Escherichia coli*.

21. The cell of claim 19, wherein the amino acid sequence is represented by (c).

22. The cell of claim 19, wherein the amino acid sequence is represented by (d).

23. A method for producing a protein having D-hydantoinase activity, the method comprising:
incubating a cell in a culture medium; and
allowing a protein having D-hydantoinase activity to be accumulated in one or both of the culture medium and the cell, wherein
the cell to be incubated being transformed with a recombinant DNA resulting from a connection of a DNA with a vector DNA, wherein
the DNA has a base sequence represented by (a) or (b) and encodes a protein having D-hydantoinase activity, wherein
(a) is the base sequence represented by SEQ ID NO: 1 in the Sequence Listing; and
(b) is a base sequence hybridizing with a complementary base sequence of the base sequence represented by SEQ ID NO: 1 in the Sequence Listing at a salt concentration corresponding to 0.1×SSC, 0.1% SDS at 60° C.

24. The method of claim 23, wherein the base sequence is represented by (a).

25. The method of claim 23, wherein the base sequence is represented by (b).

26. A method for producing a protein having D-hydantoinase activity, the method comprising:
incubating a cell in a culture medium; and
allowing a protein having D-hydantoinase activity to be accumulated in one or both of the culture medium and the cell, wherein
the cell to be incubated being transformed with a recombinant DNA resulting from a connection of a DNA with a vector DNA, wherein
the DNA encodes a protein having D-hydantoinase activity and having an amino acid sequence represented by (c) or (d), wherein
(c) is the amino acid sequence represented by SEQ ID NO: 2 in the Sequence Listing;
(d) is an amino acid sequence resulting from the substitution, deletion, insertion, addition or inversion of one to ten amino acid residues in the amino acid sequence represented by SEQ ID NO: 2 in the Sequence Listing.

27. The method of claim 26, wherein the amino acid sequence is represented by (c).

28. The method of claim 26, wherein the amino acid sequence is represented by (d).

29. A method for producing N-carbamyl-D-amino acid, the method comprising:
producing a protein having D-hydantoinase activity by incubating a cell in a culture medium; and
allowing a protein having D-hydantoinase activity to be accumulated in one or both of the culture medium and the cell; and
producing N-carbamyl-D-amino acid by making the protein having D-hydantoinase activity react with a 5-substituted hydantoin, wherein
the cell to be incubated being transformed with a recombinant DNA resulting from a connection of a DNA with a vector DNA, wherein
the DNA has a base sequence represented by (a) or (b) and encodes a protein having D-hydantoinase activity, wherein
(a) is the base sequence represented by Seq. ID No. 1 in the Sequence Listing; and
(b) is a base sequence hybridizing with a complementary base sequence of the base sequence represented by Seq. ID No. 1 in the Sequence Listing at a salt concentration corresponding to 0.1×SSC, 0.1% SDS at 60° C.

30. The method of claim 29, wherein an enzyme racemizing a 5-substituted hydantoin compound or a material containing the enzyme is allowed to react with the 5-substituted hydantoin whereby racemizing the 5-substituted hydantoin compound.

31. The method of claim 29, wherein the base sequence is represented by (a).

32. The method of claim 29, wherein the base sequence is represented by (b).

33. A method for producing N-carbamyl-D-amino acid, the method comprising:
producing a protein having D-hydantoinase activity by incubating a cell in a culture medium; and
allowing a protein having D-hydantoinase activity to be accumulated in one or both of the culture medium and the cell; and
producing N-carbamyl-D-amino acid by making the protein having D-hydantoinase activity react with a 5-substituted hydantoin, wherein
the cell to be incubated being transformed with a recombinant DNA resulting from a connection of a DNA with a vector DNA, wherein
the DNA encodes a protein having D-hydantoinase activity and having an amino acid sequence represented by (c) or (d), wherein
(c) is the amino acid sequence represented by SEQ ID NO: 2 in the Sequence Listing;
(d) is an amino acid sequence resulting from the substitution, deletion, insertion, addition or inversion of one to ten amino acid residues in the amino acid sequence represented by SEQ ID NO: 2 in the Sequence Listing.

34. The method of claim 33, wherein an enzyme racemizing a 5-substituted hydantoin compound or a material containing the enzyme is allowed to react with the 5-substituted hydantoin whereby racemizing the 5-substituted hydantoin compound.

35. The method of claim 33, wherein the amino acid sequence is represented by (c).

36. The method of claim 33, wherein the amino acid sequence is represented by (d).

37. A method for producing D-amino acid comprising:
producing a protein having D-hydantoinase activity by incubating a cell in a culture medium; and
allowing a protein having D-hydantoinase activity to be accumulated in one or both of the culture medium and the cell; and
producing D-amino acid by making the protein having D-hydantoinase activity and an enzyme hydrolyzing an N-carbamyl-D-amino acid or a material containing the enzyme react with a 5-substituted hydantoin, wherein
the cell to be incubated being transformed with a recombinant DNA resulting from a connection of a DNA with a vector DNA, wherein
the DNA has a base sequence represented by (a) or (b) and encodes a protein having D-hydantoinase activity, wherein
(a) is the base sequence represented by Seq. ID No. 1 in the Sequence Listing; and
(b) is a base sequence hybridizing with a complementary base sequence of the base sequence represented by Seq. ID No. 1 in the Sequence Listing at a salt concentration corresponding to 0.1×SSC, 0.1% SDS at 60° C.

38. The method of claim 37, wherein an enzyme racemizing a 5-substituted hydantoin compound or a material containing the enzyme is allowed to react with the 5-substituted hydantoin whereby racemizing the 5-substituted hydantoin compound.

39. The method of claim 37, wherein the base sequence is represented by (a).

40. The method of claim 37, wherein the base sequence is represented by (b).

41. A method for producing D-amino acid comprising:
producing a protein having D-hydantoinase activity by incubating a cell in a culture medium; and
allowing a protein having D-hydantoinase activity to be accumulated in one or both of the culture medium and the cell; and
producing D-amino acid by making the protein having D-hydantoinase activity and an enzyme hydrolyzing an N-carbamyl-D-amino acid or a material containing the enzyme react with a 5-substituted hydantoin, wherein
the cell to be incubated being transformed with a recombinant DNA resulting from a connection of a DNA with a vector DNA, wherein
the DNA encodes a protein having D-hydantoinase activity and having an amino acid sequence represented by (c) or (d), wherein
(c) is the amino acid sequence represented by SEQ ID NO: 2 in the Sequence Listing;
(d) is an amino acid sequence resulting from the substitution, deletion, insertion, addition or inversion of one to ten amino acid residues in the amino acid sequence represented by SEQ ID NO: 2 in the Sequence Listing.

42. The method of claim 41, wherein an enzyme racemizing a 5-substituted hydantoin compound or a material containing the enzyme is allowed to react with the 5-substituted hydantoin whereby racemizing the 5-substituted hydantoin compound.

43. The method of claim 41, wherein the amino acid sequence is represented by (c).

44. The method of claim 41, wherein the amino acid sequence is represented by (d).

* * * * *